US009506037B2

(12) United States Patent
Gerecht et al.

(10) Patent No.: US 9,506,037 B2
(45) Date of Patent: Nov. 29, 2016

(54) SELF-ORGANIZED VASCULAR NETWORKS FROM HUMAN PLURIPOTENT STEM CELLS IN A SYNTHETIC MATRIX

(71) Applicant: The Johns Hopkins University, Baltimore, MD (US)

(72) Inventors: Sharon Gerecht, Baltimore, MD (US); Sravanti Kusuma, Baltimore, MD (US)

(73) Assignee: THE JOHNS HOPKINS UNIVERSITY, Baltimore, MD (US)

( * ) Notice: Subject to any disclaimer, the term of this patent is extended or adjusted under 35 U.S.C. 154(b) by 0 days.

(21) Appl. No.: 13/844,313

(22) Filed: Mar. 15, 2013

(65) Prior Publication Data

US 2014/0273220 A1   Sep. 18, 2014

(51) Int. Cl.
| | | |
|---|---|---|
| *C12N 5/00* | (2006.01) | |
| *C12N 5/02* | (2006.01) | |
| *A61K 38/17* | (2006.01) | |
| *C07K 14/00* | (2006.01) | |
| *C12N 5/071* | (2010.01) | |

(52) U.S. Cl.
CPC ............. *C12N 5/069* (2013.01); *C12N 5/0691* (2013.01); *C12N 5/0692* (2013.01); *C12N 2501/15* (2013.01); *C12N 2501/165* (2013.01); *C12N 2501/17* (2013.01); *C12N 2501/42* (2013.01); *C12N 2506/02* (2013.01); *C12N 2506/45* (2013.01); *C12N 2533/80* (2013.01)

(58) Field of Classification Search
CPC .. C12N 5/069; C12N 5/0691; C12N 5/0692; C12N 2501/15; C12N 2501/165; C12N 2506/02; C12N 2506/45
USPC .................................. 435/377, 405; 530/356
See application file for complete search history.

(56) References Cited

U.S. PATENT DOCUMENTS

| | | |
|---|---|---|
| 2005/0112106 A1 | 5/2005 | Gerecht-Nir et al. |
| 2009/0123430 A1 | 5/2009 | De Sousa |
| 2010/0216181 A1 | 8/2010 | Daigh et al. |
| 2010/0279403 A1 | 11/2010 | Rajesh et al. |
| 2011/0305672 A1 | 12/2011 | Dalton et al. |
| 2012/0015395 A1 | 1/2012 | Shusta et al. |
| 2012/0295347 A1 | 11/2012 | Kessler |

FOREIGN PATENT DOCUMENTS

| | | |
|---|---|---|
| EP | 2277993 A1 | 1/2011 |
| WO | WO-03/010303 A1 | 2/2003 |
| WO | WO-2010/099539 A1 | 9/2010 |
| WO | 2011/021194 A2 | 2/2011 |
| WO | WO-2011/090684 A2 | 7/2011 |
| WO | WO-2011/106681 A2 | 9/2011 |
| WO | WO-2012/006440 A2 | 1/2012 |
| WO | WO-2012/168167 A1 | 12/2012 |

OTHER PUBLICATIONS

Allegrucci et al., 2006, Human Reproduction Update, Vol. Advance Access published on Aug. 26, 2006, p. 1-18.*
Sato et al., 2003, Developmental Biology, vol. 260, p. 404-413.*
Abeyta et al., 2004, Human Molecular Genetics, vol. 13, No. 6, p. 601-608.*
Kusuma et al., 2013, PNAS, vol. 110, No. 31, p. 12601-12606.*
Seifert et al., 2008, Differentiation, vol. 76, p. 857-867.*
Gerecht-Nir et al., 2004, Biology of Reproduction, vol. 71, p. 2029-2036.*
Dalton et al., 2011, US 20110305672 A1.*
Abaci et al., (2011). Unforeseen decreases in dissolved oxygen levels affect tube formation kinetics in collagen gels. American Journal of Physiology—Cell Physiology 301, C431-C440.
Airas et al., (1995). CD73 is involved in lymphocyte binding to the endothelium: characterization of lymphocyte-vascular adhesion protein 2 identifies it as CD73. The Journal of Experimental Medicine 182, 1603-1608.
Bardin et al., (2001). Identification of CD146 as a component of the endothelial junction involved in the control of cell-cell cohesion. Blood 98, 3677-3684.
Cheng et al., (2012). Low Incidence of DNA Sequence Variation in Human Induced Pluripotent Stem Cells Generated by Nonintegrating Plasmid Expression. Cell Stem Cell 10, 337-344.
Chou et al., (2011). Efficient human iPS cell derivation by a non-integrating plasmid from blood cells with unique epigenetic and gene expression signatures. Cell Research 21, 518-529.
Crisan et al., (2012). Perivascular cells for regenerative medicine. Journal of Cellular and Molecular Medicine, 2851-2860.
Crisan et al., (2008). A Perivascular Origin for Mesenchymal Stem Cells in Multiple Human Organs. Cell Stem Cell 3, 301-313.
Dar et al., (2011). Multipotent Vasculogenic Pericytes From Human Pluripotent Stem Cells Promote Recovery of Murine Ischennic Limb / Clinical Persepective. Circulation 125, 87-99.
Dickinson et al., (2010). Guiding endothelial progenitor cell tube formation using patterned fibronectin surfaces. Soft Matter 6, 5109-5119.
Discher et al., (2009). Growth Factors, Matrices, and Forces Combine and Control Stem Cells. Science 324, 1673-1677.
Drukker et al., (2012). Isolation of primitive endoderm, mesoderm, vascular endothelial and trophoblast progenitors from human pluripotent stem cells. Nature Biotechnology 30, 531-542.
Duff et al., (2003). CD105 is important for angiogenesis: Evidence and potential applications. FASEB Journal 17, 984-992.
Ferreira et al., (2007). Vascular progenitor cells isolated from human embryonic stem cells give rise to endothelial and smooth muscle-like cells and form vascular networks in vivo. Circulation Research 101, 286-294.

(Continued)

*Primary Examiner* — Shin Lin Chen
(74) *Attorney, Agent, or Firm* — Johna Hopkins Tech Ventures

(57) ABSTRACT

A bicellular vascular population derived from human pluripotent stem cells (hPSCs) undergoes morphogenesis and assembly in a synthetic hydrogel. It is shown that hPSCs can be induced to co-differentiate into early vascular cells (EVCs) in a clinically-relevant strategy dependent upon Notch activation. These EVCs mature into ECs and pericytes, and self-organize to form vascular networks in an engineered matrix. Upon in vivo implantation, multicellular human vascular networks are functionally perfused. Thus, a derived bicellular population is exploited for its intrinsic self-assembly capability to create functional microvasculature in a deliverable matrix.

15 Claims, 19 Drawing Sheets

(56) References Cited

OTHER PUBLICATIONS

Grayson et al., (2010). Engineering anatomically shaped human bone grafts. Proceedings of the National Academy of Sciences of the United States of America 107, 3299-3304.

Haase et al., (2009). Generation of Induced Pluripotent Stem Cells from Human Cord Blood. Cell Stem Cell 5, 434-441.

Hanjaya-Putra et al., (2011). Controlled activation of morphogenesis to generate a functional human microvasculature in a synthetic matrix. Blood 118, 804-815.

Hofmann et al., (2007). Notch Signaling in Blood Vessels: Who Is Talking to Whom About What? Circulation Research 100, 1556-1568.

James et al., (2010). Expansion and maintenance of human embryonic stem cell-derived endothelial cells by TGFb inhibition is !di dependent. Nature Biotechnology 28, 161-166.

Kang et al., (2011). Bioengineered human vascular networks transplanted into secondary mice reconnect with the host vasculature and re-establish perfusion. Blood. 6718-6721.

Khetan et al., (2010). Patterning network structure to spatially control cellular remodeling and stem cell fate within 3-dimensional hydrogels. Biomaterials 31, 8228-8234.

Khetan et al., (2009). Sequential crosslinking to control cellular spreading in 3-dimensional hydrogels. Soft Matter 5, 1601-1606.

Kusuma et al., (2012). The extracellular matrix is a novel attribute of endothelial progenitors and of hypoxic mature endothelial cells. The FASEB Journal. 4925-4936.

Lee et al., (2010). Derivation of neural crest cells from human pluripotent stem cells. Nat Protocols 5, 688-701.

Mali et al., (2010). Butyrate greatly enhances derivation of human induced pluripotent stem cells by promoting epigenetic remodeling and the expression of pluripotency-associated genes. Stem Cells 28, 713-720.

Mead et al., (2007). Isolation and Characterization of Endothelial Progenitor Cells from Human Blood. In Current Protocols in Stem Cell Biology (John Wiley & Sons, Inc.). Supplement 6, Unit 2C.1.

Orlidge et al., (1987). Inhibition of capillary endothelial cell growth by pericytes and smooth muscle cells. The Journal of Cell Biology 105, 1455-1462.

Park et al., (2010). Efficient differentiation of human pluripotent stem cells into functional CD34+ progenitor cells by combined modulation of the MEK/ERK and BMP4 signaling pathways. Blood 116, 5762-5772.

Pittenger et al., (1999). Multilineage potential of adult human mesenchymal stem cells. Science 284, 143-147.

Sainson et al., (2008). Regulation of angiogenesis by homotypic and heterotypic notch signalling in endothelial cells and pericytes: from basic research to potential therapies. Angiogenesis 11, 41-51.

Stewart et al., (2011). Delta-like ligand 4-Notch signaling regulates bone marrow-derived pericyte/vascular smooth muscle cell formation. Blood 117, 719-726.

Stratman et al., (2009a). Pericyte recruitment during vasculogenic tube assembly stimulates endothelial basement membrane matrix formation. Blood 114, 5091-5101.

Stratman et al., (2009b). Endothelial cell lumen and vascular guidance tunnel formation requires MT1-MMP-dependent proteolysis in 3-dimensional collagen matrices. Blood 114, 237-247.

Thomson, J.A. (1998). Embryonic stem cell lines derived from human blastocysts. Science 282, 1145-1147.

Vo et al., (2010). Smooth-MuscleLike Cells Derived from Human Embryonic Stem Cells Support and Augment Cord-Like Structures In Vitro. Stem Cell Reviews and Reports 6, 237-247.

Vodyanik et al., (2010). A mesoderm-derived precursor for mesenchymal stem and endothelial cells. Cell Stem Cell 7, 718-729.

Vunjak-Novakovic et al., (2011). Biomimetic Platforms for Human Stem Cell Research. Cell Stem Cell 8, 252-261.

Wang et al., (2007). Endothelial cells derived from human embryonic stem cells form durable blood vessels in vivo. Nat Biotech 25, 317-318.

Wanjare et al., (2012). Derivation and maturation of synthetic and contractile vascular smooth muscle cells from human pluripotent stem cells. Cardiovascular Research. 321-330.

Yang et al., (2008). Human cardiovascular progenitor cells develop from a KDR+ embryonic-stem-cell-derived population. Nature 453, 524-528.

Zou et al., (2011). Site-specific gene correction of a point mutation in human iPS cells derived from an adult patient with sickle cell disease. Blood 118, 4599-4608.

Ahmad et al., "Cross-correlation-based image acquisition technique for manually-scanned optical coherence tomography," Opt. Express 17(10), 8125-8136 (2009).

Aikawa et al. (1993) Circ Res 107,2085-8.

Au P et al. "Bone marrow derived mesenchymal stem cells facilitate engineering of long-lasting functional vasculature", Blood, 2008, vol. 111, pp. 4551-4558.

Au P et al. "Differential in vivo potential of endothelial progenitor cells from human umbilical cord blood and adult peripheral blood to form functional long-lasting vessels" Blood, 2007, vol. 111, pp. 1302-1305.

Ball et al., Platelet-derived growth factor receptors regulate mesenchymal stem cell fate: implications for neovascularization. Expert Opin Biol Ther 2010;10:57-71.

Beamish et al., Molecular regulation of contractile smooth muscle cell phenotype: implications for vascular tissue engineering. Tissue Eng Part B Rev. 2010;16:467-491.

Becker et al., "State estimation and feedforward tremor suppression for a handheld micromanipulator with a Kalman filter," IEEE/RSJ, International Conference on Intelligent Robots and Systems, 5160-6165(2011).

Bertolino et al., Transforming Growth Factor-β Signal Transduction in Angiogenesis and Vascular Disorders. Chest 2005;128:585S-590S.

Bettinger et al. "Enhancement of In Vitro Capillary Tube Formation by Substrate Nanotopography", Adv. Mater, 2008, vol. 20, pp. 99-103.

Boppart et al., "Forward-imaging instruments for optical coherence tomography," Opt. Lett. 22 (21), 1618-1620 (1997).

Boppart et al., "Intraoperative assessment of microsurgery with three-dimensional optical coherence tomography," Radiology, vol. 208, pp. 81-86, 1998.

Boppart et al., "Optical coherence tomography: feasibility for basic research and image-guided surgery of breast cancer," Breast Cancer Res. Treatment 84(2), 85-97(2004).

Carmeliet P. "Mechanisms of Angiogenesis and Arteriogenesis", Nat. Med, 2000, vol. 6, pp. 389-395.

Carmeliet, P. "Angiogenesis in health and disease" Nature Medicine, 2003, vol. 9, pp. 653-660.

Caspi et al. "Tissue engineering of vascularized cardiac muscle from human embryonic stem cells" Circ Res, 2007, vol. 100, pp. 263-272.

Cecchettini et al., Chapter Two—Vascular Smooth-Muscle-Cell Activation: Proteomics Point of View. In: Kwang WJ, ed. International Review of Cell and Molecular Biology. Vol vol. 288: Academic Press; 2011:43-99.

Chan-Park et al., Biomimetic control of vascular smooth muscle cell morphology and phenotype for functional tissue-engineered small-diameter blood vessels. J Biomed Mater Res A 2009;88A:1104-1121.

Chen et al., "Noninvasive imaging of in vivo blood flow velocity using optical Doppler tomography," Opt. Lett. 22(14), 1119-1121(1997).

Chen et al., Myocardin: a component of a molecular switch for smooth muscle differentiation. J Mol Cell Cardiol. 2002;34:1345-1356.

Chen et al. "Transforming growth factor-beta-induced differentiation of smooth muscle from a neural crest stem cell line", Circulation Research, 2004, vol. 94, pp. 1195-1202.

Chou et al., Efficient human iPS cell derivation by a non-integrating plasmid from blood cells with unique epigenetic and gene expression signatures. Cell Res 2011;21:518-529.

(56) References Cited

OTHER PUBLICATIONS

Darland et al., TGFP is required for the formation of capillary-like structures in three-dimensional cocultures of 1011/2 and endothelial cells. Angiogenesis 2001;4;11-20.
Dempsey et al., Enhanced growth capacity of neonatal pulmonary artery smooth muscle cells in vitro: Dependence on cell size, time from birth, insulin-like growth factor I, and auto-activation of protein Kinase C. J Cell Physiol 1994;160:469-481.
Ding Ret al. "Endothelial-mesenchymal interactions in vitro reveal molecular mechanisms of smooth muscle/pericyte differentiation" Stem Cells and Development, 2004, vol. 13, pp. 509-520.
Dingemans et al., Extracellular matrix of the human aortic media: An ultrastructural histochemical and immunohistochemical study of the adult aortic media. Anat Rec 2000;258:1-14.
Doi et al., "Notch signaling regulates the differentiation of bone marrow-derived cells into smooth muscle-like cells during arterial lesion formation" Biochemical and Biophysical Communications, vol. 381, pp. 654-659 (Feb. 27, 2009).
Duband et al. "Calponin and SM 22 as differentiation markers of smooth muscle: spatiotemporal distribution during avian embryonic development", Differentiation, 1993, vol. 55, pp. 1-11.
Duncan et al., "Processing algorithms for tracking speckle shifts in optical elastography of biological tissues," J. Biomed. Opt. 6(4), 418-426(2001).
Extended European Search Report issued in European Patent Application No. 11748168.9 dated Aug. 28, 2013.
Folkman et al. "Long-term culture of capillary endothelial cells", PNAS USA, 1979, vol. 76, pp. 5217-5221.
Ford et al., "PKH26 and 125I-PKH95: characterization and efficacy as labels for in vitro and in vivo endothelial cell localization and tracking," J. Surg. Res., vol. 62, pp. 23-28. (1996).
Freshney, R. Ian (Culture of Animal Cells: A manual of Basic Techniques and Specialized Applications, 6th ed. Wiley Blackwell, 2011. pp. 163-186.
Gaengel et al., Endothelial-Mural Cell Signaling in Vascular Development and Angiogenesis. Arterioscler Thromb Vasc Biol 2009;29:630-638.
Gerecht-Nir et al. "Human Embryonic Stem Cells as an In Vitro Model for Human Vascular Development and the Induction of Vascular Differentiation", Laboratory Investigation, 2003, vol. 83, pp. 1811-1820.
Gong et al. "Small-diameter human vessel wall engineered from bone marrow-derived mesenchymal stem cells (hMSCs)", FASEB Journal, 2008, vol. 22, pp. 1635-1648.
Gong et al. "Influence of culture medium on smooth muscle cell differentiation from human bone marrow-derived mesenchymal stem cells" Tissue Engineering-Part A, 2009, vol. 15, pp. 319-330.
Grainger et al., Transforming growth factor-beta dynamically regulates vascular smooth muscle differentiation in vivo. J Cell Sci 1998;111:2977-2988.
Ha et al., "Compensation of motion artifacts in catheter-based optical frequency domain imaging," Opt. Express 18(11), 11418-11427 (2010).
Han et al., "Handheld forward-imaging needle endoscope for ophthalmic optical coherence tomography inspection," J. Biomed. Opt. 13(2), 020505(2008).
Hanjaya-Putra et al. "Vascular endothelial growth factor and substrate mechanics regulate in vitro tubulogenesis of endothelial progenitor cells", J Cell Mol Med, 2009, vol. 14, No. 10, pp. 2436-2447.
Hellstrom et al., Role of PDGF-B and PDGFR-beta in recruitment of vascular smooth muscle cells and pericytes during embryonic blood vessel formation in the mouse. Development 1999;126:3047-3055.
Hill et al., "Human Embryonic Stem Cell Derived Vascular Progenitor Cells Capable of Endothelial and Smooth Muscle Cell Function", Experimental Hematology, vol. 38, No. 3, pp. 246-257. (2010).
Hirschi et al. Smooth Muscle Stem Cells:, Anatomical Record-Par A Discoveries in Molecular, Cellular, and Evolutionary Biology, 2004, vol. 276, pp. 22-33.
Hirschi et al. "PDGF, TGF-62 , and Heterotypic Cell-Cell Interactions Mediate Endothelial Cell-induced Recruitment of 10T1/2 Cells and Their Differentiation to a Smooth Muscle Fate", Journal of Cell Biology, 1998, vol. 252, pp. 805-814.
Hirschi et al. "Assessing Identity, phenotype, and fate of endothelial progenitor cells", Arteriosclerosis, Thrombosis, and Vascular Biology, 2008, vol. 28, pp. 1584-1595.
Hirschi et al. "Pericytes in the microvasculature" Cardiovascular Research, 1996, vol. 32, pp. 687-698.
Hoofnagle et al., Myocardin is differentially required for the development of smooth muscle cells and cardiomyocytes. Am J Physiol Heart Circ Physiol 2011;300:H1707-1721.
Huang et al., "Motion compensated fiber-optic confocal microscope based on a common-path optical coherence tomography distance sensor," Opt. Eng. 50(8), 083201 (2011).
Huang et al., "Noncontact common-path Fourier domain optical coherence tomography method for in vitro intraocular lens power measurement", J. Biomed. Opt. 16(12), 126005(2011).
Huang et al., "Optical coherence tomography," Science, 254(5035), 1178-1181(1991).
Huang et al., "Real-time 3D and 4D Fourier domain Doppler optical coherence tomography based on dual graphics processing units," Biomed. Opt. Express 3(9), 2162-2174 ( 2012).
Huang et al., Differentiation of human embryonic stem cells into smooth muscle cells in adherent monolayer culture. Biochem Biophys Res Commun 2006;351:321-327.
Huo et al., "Forward-viewing resonant fiber-optic scanning endoscope of appropriate scanning speed for 3D OCT imaging," Opt. Express 18(14),14375-14384(2010).
Iftimia et al., "Adaptive ranging for optical coherence tomography," Opt. Express 12(17), 4025-4034 (2004).
Ingram et al. "Identification of a novel hierarchy of endothelial progenitor cells using human peripheral and umbilical cord blood" Blood, 2004, vol. 104, pp. 2752-2760.
International Search Report dated Jun. 27, 2013, issued in International Application No. PCT/US2013/028341.
International Search Report issued in PCT Application No. PCT/US2011/026294 dated Nov. 9, 2011.
International Search Report issued in PCT Application No. PCT/US2014/030708 dated Jul. 24, 2014.
Izzard et al., Mechanisms underlying maintenance of smooth muscle cell quiescence in rat aorta: role of the cyclin dependent kinases and their inhibitors. Cardiovasc Res 2002;53:242-252.
Jafri et al., "Optical coherence tomography guided neurosurgical procedures in small rodents," J. Neurosci. Methods 176(2), 85-89 (2009).
Jain RK. "Molecular regulation of vessel maturation", Nature Medicine, 2003, vol. 9, pp. 685-693.
Jin et al., Notch signaling regulates platelet-derived growth factor receptor-beta expression in vascular smooth muscle cell. Circ Res 2008;102:1483-1491.
Jung et al., "Three-dimensional optical coherence tomography employing a 2-axis microelectromechanical scanning mirror," IEEE J. Sel. Top. Quantum Electron. 11(4), 806-810(2005).
Kang et al., "Endoscopic functional Fourier domain common path optical coherence tomography for microsurgery," IEEE J. Sel. Top. Quantum Electron. 16(4), 781-792(2010).
Kang et al., "Real-time three-dimensional Fourier-domain optical coherence tomography video image guided microsurgeries," J. Biomed. Opt. 17(8), 081403 (2012).
Karnik et al., A critical role for elastin signaling in vascular morphogenesis and disease. Development. 2003;130:411-423.
Kaufman et al. "Hematopoietic colony-forming cells derived from human embryonic stem cells" PNAS USA, 2001, vol. 98, pp. 10716-10721.
Klein et al., "Megahertz OCT for ultrawide-field retinal imaging with a 1050nm Fourier domain mode-locked laser," Opt. Express, vol. 19, pp. 3044-3062, 2011.

(56) References Cited

OTHER PUBLICATIONS

Kobayash et al., "Mechanical Stress Promotes the Expression of Smooth Muscle-Like Properties in Marrow Stromal Cells", Experimental Hematology, vol. 32, pp. 1238-1245. (2004).
Koike et al. "Tissue engineering: creation of long-lasting blood vessels" Nature, 2004, vol. 428, pp. 138-139.
Kuprinski et al., "Transforming Growth Factor-B and Notch Signaling Mediate Stem Cell Differentiation Into Smooth Muscle Cells", Stem Cells, vol. 28, pp. 734-742. (2010).
Kuro-o et al. "Developmentally regulated expression of vascular smooth muscle myosin heavy chain isoforms", Journal of Biological Chemistry, 1989, vol. 264, pp. 18272-18275.
Lee et al., "Motion correction for phase-resolved dynamic optical coherence tomography imaging of rodent cerebral cortex," Biomed. Opt. Express 19(22), 21258-21270 (2012).
Lee et al., Functional Recapitulation of Smooth Muscle Cells Via Induced Pluripotent Stem Cells From Human Aortic Smooth Muscle Cells. Circ Res 2010;106:120-128.
Leitgeb et al., "Ultrahigh resolution Fourier domain optical coherence tomography," Opt. Express 12(10), 2156-2165(2004).
Levenberg et al. Endothelial cells derived from human embryonic stem cells PNAS USA, 2002, vol. 99, pp. 4391-4396.
Levenberg S., et al., Blood, 110, 805-814 (2007).
Lindskog et al. "New insights to vascular smooth muscle cell and pericyte differentiation of mouse embryonic stem cells in vitro" Arterioscler Thromb Vasc Biol, 2006, vol. 26, pp. 1457-1464.
Liu et al., "Distortion-free freehand-scanning OCT implemented with real-time scanning speed variance correction," Opt. Express 20(15), 16567-16583 (2012).
Lombardi et al., Methodologic considerations important in the accurate quantitation of aortic smooth muscle cell replication in the normal rat. Am J Pathol. 1991;138:441-446.
Maguluri et al., "Three dimensional tracking for volumetric spectral-domain optical coherence tomography," Opt. Express 15(25), 16808-16817 ( 2007).
Melero-Martin JM et al. "Engineering robust and functional vascular networks in vivo with human adult and cord blood-derived progenitor cells", Circulation Research, 2008, vol. 103, pp. 194-202.
Mulvany et al., Structure and function of small arteries. Physiol Rev 1990;70:921-961.
Narazaki G et al. "Directed and systematic differentiation of cardiovascular cells from mouse induced pluripotent stem cells" Circulation, 2008, vol. 118, pp. 498-506.
Nishikawa et al. "Progressive lineage analysis by cell sorting and culture identifies FLK1=VE-cadherin+ cells at a diverging point of endothelial and hemopoietic lineages." Development, 125, 1747-1757 (1998).
Nourse et al., "VEGF Induces Differentiation of Functional Endothelium From Human Embryonic Stem Cells", Cell Biology/Signaling, vol. 30, pp. 80-89. (2009).
Owens et al., Molecular Regulation of Vascular Smooth Muscle Cell Differentiation in Development and Disease. Physiol Rev 2004;84:767-801.
Oyamada et al., Transplantation of vascular cells derived from human embryonic stem cells contributes to vascular regeneration after stroke in mice. J Transl Med. 2008;6:54.
Parmacek et al., Transcriptional programs regulating vascular smooth muscle cell development and differentiation. Curr Top Dev Biol Vol vol. 51: Academic Press:69-89.
Patel et al., Elastin biosynthesis: The missing link in tissue-engineered blood vessels. Cardiovasc Res 2006;71:40-49.
Peerani et al. "Niche-mediated Control of Human Embryonic Stem Cell self-renewal and Differentiation." The EMBO Jounal (2007) 26, 4744-4755.
Pertoft, H. "Fractionation of cells and subcellular particles with Percoll", J. Biocchem Biophys Methods, 2000; vol. 44, pp. 1-30.
Phelps et al., Update on therapeutic vascularization strategies. Regen Med 2009;4:65-80.
Potsaid et al., "Ultrahigh speed Spectral / Fourier domain OCT ophthalmic imaging at 70,000 to 312,500 axial scans per second," Opt. Express, vol. 16, pp. 15149-15169, 2008.
Potta et al. "Functional characterization and transcriptome analysis of embryonic stem cell derived contractile smooth muscle cells" Hypertension, 2009, vol. 53, pp. 196-204.
Prater et al. "Working hypothesis to redefine endothelial progenitor cells" Leukemia, 2007, vol. 21, pp. 1141-1149.
Rensen et al. "Regulation and characteristics of vascular smooth muscle cell phenotypic diversity" Netherlands Hear Journal, 2007, vol. 15, pp. 100-108.
Reubinoff et. Al. "Embryonic stem cell lines from human blastocysts: somatic differentiation in vitro," Nature Biotechnology, 2000, vol. 18, No. 4, pp. 399-404.
Rodriguez et al. "Clonogenic multi potent stem cells in human adipose tissue differentiate into functional smooth muscle cells". PNAS USA, 2006, vol. 103, pp. 12167-12172.
Schenke-Layland et al., Reprogrammed Mouse Fibroblasts Differentiate into Cells of the Cardiovascular and Hematopoietic Lineages. Stem cells 2008;26:1537-1546.
Shah et al. "Alternative neural crest cells fates are instructively promoted by TGD-Beta superfamily members" Cell, 1996, vol. 85, pp. 331-343.
Shuldiner et al. "Effects of eight growth factors on the differentiation of cells derived from human embryonic stem cells", 2000, PNAS USA, vol. 97, pp. 11307-11312.
Singh et al., "Physiological tremor during retinal microsurgery," Proc. 28th Annual Conf. IEEE Eng. Med. Bio. Soc.,171-172(2002).
Sinha et al. "Assessment of contractility of purified smooth muscle cells derived from embryonic stem cells" Stem Cells, 2006, vol. 24, pp. 1678-1688.
Sinha et al., Transforming growth factor-beta1 signaling contributes to development of smooth muscle cells from embryonic stem cells. Am J Physiol Cell Physiol. 2004;287:C1560-1568.
Sobue et al., Expressional regulation of smooth muscle cell-specific genes in association with phenotypic modulation. Molecular and Cellular Biochemistry 1999;190:105-18.
Solan et al. "Age effects on Vascular Smooth muscle: An engineered tissue approach" Cell Transplantation, 2005, vol. 14, pp. 481-488.
Sone et al. "Different differentiation kinetics of vascular progenitor cells in primate and mouse embryonic stem cells" Circulation, 2003, vol. 107, pp. 2085-2088.
Sone et al. "Pathway for Differentiation of Human Embryonic Stem Cells to Vascular Cell Components and Their Potential for Vascular Regeneration", Arterioscler Thromb. Vasco Biol., 2007, vol. 27, pp. 2127-2134.
Song et al., "Active tremor cancellation by a "Smart" handheld vitreoretinal microsurgical tool using swept source optical coherence tomography," Opt. Express 20, 23414-23421 (2012).
Stewart et al. "Deconstructing Human Embryonic Stem Cell Cultures: Niche Regulation of Self-Renewal and Pluripotency." J. Mol. Med. (2008) 86:875-86.
Sugiyama et al., "Characterization of smooth muscle-like cells in circulating human peripheral Blood", Atherosclerosis, 2006, vol. 187, pp. 351-362.
Swistowski et al, Efficient Generation of Functional Dopaminergic Neurons from Human Induced Pluripotent Stem Cells Under Defined Conditions. Stem Cells, 28, 1893-1904 (2010).
Takahashi et al., Induction of Pluripotent Stem Cells from Adult Human Fibroblasts by Defined Factors. Cell 2007;131:861-872.
Tan et al., "In-fiber common-path optical coherence tomography using a conical-tip fiber," Opt. Express 17(4),2375-2380(2009).
Taura et al. "Induction and isolation of vascular cells from human induced pluripotent stem cells-brief report", Arterioscler Thromb Vasc Biol, 2009, vol. 29, pp. 1100-1103.
Thyberg J. Differences in caveolae dynamics in vascular smooth muscle cells of different phenotypes. Lab Invest 2000;80:915-929.
Timmermans et al. "Endothelial progenitor cells: Identity defined?" Journal of Cellular and Molecular Medicine, 2009, vol. 13, pp. 87-102.
Traktuev et al. "A population of multipotent CD34-positive adipose stromal cells share pericyte and mesenchymal surface markers,

(56) References Cited

OTHER PUBLICATIONS reside in a perlendothelial location, and stabilize endothelial networks", Circulation Research, 2008, vol. 102, pp. 77-85.
Tsai et al. "Shear Stress Induces Synthetic-to-Contractile Phenotypic Modulation in Smooth Muscle Cells via Peroxisome Proliferator-Activated Receptor (alpha)/(delta) Activations by Prostacyclin Released by Sheared Endothelial Cells" Circ Res, 2009, vol. 105, pp. 471-480.
Tuna et al., Smooth Muscle Biomechanics and Plasticity: Relevance for Vascular Calibre and Remodelling. Basic Clin Pharmacol Toxicol 2012;110:35-41.
Vakhtin et al., "Common-path interferometer for frequency-domain optical coherence tomography," App. Opt. 42(34), 6935-6958 (2003).
van Kooten et al., "Fluid Shear Induced Endothelial Cell Detachment From Modified Polystyrene Substrata", Colloids and Surfaces B: Biointerfaces, vol. 3, No. 3, pp. 147-158. (1994).
Vazao et al., Towards the maturation and characterization of smooth muscle cells derived from human embryonic stem cells. PLoS One.2011;6:e17771.
Vodyanik et al, Current protocols in cell biology, Chapter 23 (2007).
Wang et al., Activation of cardiac gene expression by myocardin, a transcriptional cofactor for serum response factor. Cell 2001;105:851-862.
Wang et al. "Human Embryonic Stem Cells Maintained in the Absence of Mouse Embryonic Fibroblasts or Conditioned Media are Capable of Hematopietic Development." Blood 2005 105: 4598-4603.
Wang et al., Myocardin is a master regulator of smooth muscle gene expression. Proc Natl Acad Sci U S A 2003;100:7129-7134.
Wolinsky et al., A Lamellar Unit of Aortic Medial Structure and Function in Mammals. Circ Res 1967;20:99-111.
Woodford et al., "Tissue engineering 2.0: guiding self-organization during pluripotent stem cell differentiation," Current Opinion in Biotechnology, 2012, vol. 23, pp. 810-819.
Xiao et al., Stem cell-derived Sca-1+ progenitors differentiate into smooth muscle cells, which is mediated by collagen IV-integrin α1/β1/αv and PDGF receptor pathways. Am J Physiol Cell Physiol 2007;292:C342-C352.
Xie et al., Yap1 Protein Regulates Vascular Smooth Muscle Cell Phenotypic Switch by Interaction with Myocardin. J Biol Chem 2012;287:14598-14605.
Xie et al. "A comparison of murine smooth muscle cells generated from embryonic versus induced pluripotent stem cells" Stem Cells Dev, 2009, vol. 18, pp. 741-748.
Xie et al., "A Highly Efficient Method to Differentiate Smooth Muscle Cells Form Human Embryonic Stem Cells," Arteriosclerosis, Thrombosis, and Vascular Biology, vol. 27, No. 12, 2007, pp. e311-e312.
Xie et al., Smad3-mediated Myocardin Silencing. J Biol Chem 2011;286:15050-15057.
Xu et al., Pulmonary artery smooth muscle cells from chronically hypoxic neonatal calves retain fetal-like and acquire new growth properties. Am J Physiol Lung Cell Mol Physiol 1997;273:L234-L245.
Yamamoto et al., Type I Collagen Promotes Modulation of Cultured Rabbit Arterial Smooth Muscle Cells from a Contractile to a Synthetic Phenotype. Exp Cell Res 1993;204:121-129.
Yamashita et al., Flk1-positive cells derived from embryonic stem cells serve as vascular progenitors. Nature. 2000;408:92-96.
Yu et al., "Oxidized low density lipoprotein-induced transdifferentiation of bone marrow-derived smooth muscle-like cells into foam-like cells in vitro" International Journal of Experimental Pathology, vol. 91, pp. 24-33 (Dec. 22, 2009).
Zhang et al., "Common-path low-coherence interferometry fiber-optic sensor guided microincision," J. Biomed. Opt. 16(9),095003(2011).
Zhang et al., "Real-time intraoperative 4D full-range FD-OCT based on the dual graphics processing units architecture for microsurgery guidance," Biomed. Opt. Express. 2(4), 764-770 (2011).
Zysk et al., "Optical coherence tomography: a review of clinical development from bench to bedside," J. Biomed. Opt. 12(5), 051403 (2007).
Extended European Search Report issued in European Patent Application No. 13754938.2 dated Jul. 17, 2015.
Hashemi et al., "The promotion of stemness and pluripotency following feeder-free culture of embryonic stem cells on collagen-grafted 3-dimensional nanofibrous scaffold," Biomaterials, vol. 32, No. 30, 2011, pp. 7363-7374.
Extended European search report dated Jul. 26, 2016 for EP application 14763516.3.
Crisan, M., et al., "Perivascular cells for regenerative medicine", Journal of Cellular and Molecular Medicine, vol. 16, No. 12, pp. 2851-2860, Dec. 1, 2012.
Dar, A., et al., "Multipotent vasculogenic pericytes from human pluripotent stem cells promote recovery of murine schemic limb", Circulation, vol. 125, No. 1, pp. 87-99, Jan. 3, 2012.
Hanjaya-Putra, D., et al., "Controlled activation of morphogenesis to generate a functional human microvasculature in a synthetic matrix", Blood, vol. 118, No. 3, pp. 804-815, Apr. 28, 2011.
James, D., et al., "Expansion and maintenance of human embryonic stem cell-derived endothelial cells by TGF[beta] Inhibition is Id1 dependent", Nature Biotechnology, vol. 28, No. 2, pp. 161-166, Feb. 1, 2010.
<Kusuma, S., et al., "Self-organized vascular networks from human pluripotent stem cells in a synthetic matrix", PNAS, vol. 110, No. 31, pp. 12601-12606, Jul. 15, 2013.
Nonaka, H., et al., "Development of stabilin2+ endothelial cells from mouse embryonic stem cells by inhibition of TGF [beta]/signaling", Biochemical and Biophysical Research Communications, Academic Press Inc. Orlando, FL, US, vol. 375, No. 2, pp. 256-260, Oct. 17, 2008.

* cited by examiner

US 9,506,037 B2

SELF-ORGANIZED VASCULAR NETWORKS FROM HUMAN PLURIPOTENT STEM CELLS IN A SYNTHETIC MATRIX

U.S. GOVERNMENT SUPPORT

The present invention was partially supported by the following grants: NIH grant F31HL112644, NIH grant 2R01HL073781, NIH grant R01HL107938 and NIH grant U54CA143868 and National Science Foundation grant 1054415; the United States government may have right to this invention.

CROSS-REFERENCE TO PRIOR APPLICATIONS

N/A

BACKGROUND OF THE INVENTION

Area of the Art

The present invention is in the area of pluripotent stem cells and more particularly deals with a method to differentiate a vascular network from stem cells.

Description of the Background Art

Perhaps the greatest roadblock to the success of tissue regenerative therapies is the establishment of a functional microvascular network to support tissue survival and growth (Discher et al., 2009). Microvascular construction or regeneration depends on endothelial morphogenesis into a three-dimensional, tubular network followed by stabilization of the assembling structures by recruited pericytes (Hanjaya-Putra et al., 2011; Stratman et al., 2009a). To create such a construct for therapeutic applications, patient-derived ECs and pericytes must be incorporated into a synthetic matrix, which confers the advantage to control and modulate vascular morphogenesis and simultaneously represents a clinically-relevant construct in which to deliver the engineered microvascular networks to in vivo environments (Vunjak-Novakovic and Scadden, 2011).

Human pluripotent stem cells (hPSCs), including human embryonic stem cells (hESCs) and human induced PSCs (hiPSCs), offer the opportunity to derive EVCs from the same source, the latter of which offers patient specificity. Various cell markers have been proposed to identify vascular precursors (of ECs and pericytes) from differentiating hPSCs including CD34 (Ferreira et al., 2007; Park et al., 2010), KDR/VEGFR2 (Yang et al., 2008), and apelin receptor (Vodyanik et al., 2010). Purification of such progenitors is required from an uncontrolled differentiated cell population (i.e. via embryoid body [EB] formation or co-culture on mouse feeder layer) through marker enrichment or selection through genetic manipulation. Importantly, none of these derived cells have been demonstrated to self-assemble into functional microvasculature containing both ECs and pericytes.

Current approaches for the differentiation of hPSCs toward the vascular lineage build on the notion that a purified, single derivative—either a progenitor or matured cell type—is obligatory for the generation of functional vasculature. These approaches stem from the necessity to eliminate differentiation to undesirable lineages as well as to better understand the development of the vasculature. Indeed, from this body of work, it has become apparent that various cell markers and biochemical cues can be used to guide differentiation and derive functional ECs (Drukker et al., 2012; Ferreira et al., 2007; James et al., 2010; Wang et al., 2007), vascular smooth muscle cells (Drukker et al., 2012; Ferreira et al., 2007; Wanjare et al., 2012) and pericytes (Dar et al., 2011). Here we disclose a new conceptual approach in which the cells of the microvasculature are derived in a single, bipotent type population. The developed protocol employs a monolayer culture and avoids an EB intermediate and sorting, thereby ensuring reproducibility and clinical applicability. The derived bipotent population is able to work synergistically to recreate the tissue. Thus, we harness intrinsic tissue-level differentiation and self-assembly capabilities toward the translational realization of hPSCs. This new paradigm could prove useful for the construction of other multicellular tissues for regeneration.

The current disclosure demonstrates that hPSCs can be induced to differentiate into early derivatives of the vascular lineage (i.e. EVCs) that comprise the microvascular architecture without a specific differentiation-inducible feeder layer, EB formation, or genetic manipulation, and that such EVCs can mature into ECs and pericytes and can self-assemble to form functional vascular networks in an engineered matrix.

The ability to derive a multi-cell type population, which is then leveraged to form physiologically- and clinically-relevant vascular networks that are functionally perfused in vivo, is dependent upon activation of Notch signaling. Inhibition of Notch signaling promoted EC differentiation as depicted via VEcad enrichment. This discovery provides the groundwork for future studies into the importance of Notch signaling in in vitro vascular co-differentiation strategies. Our novel bicellular constructs represent a fundamental advancement to the future of cell-based therapies The balance between commitment and plasticity of the EVCs specifically within the vascular lineage allows for vascular fate and functional network maturation. This controlled system is reproducible, generates physiologically relevant vascular networks in implantable matrices, and thus presents the next fundamental step toward patient-specific engineered tissue with clinically translatable potential.

BRIEF DESCRIPTION OF THE FIGURES

The patent or application file contains at least one drawing executed in color. Copies of this patent or patent application publication with color drawing(s) will be provided by the Office upon request and payment of the necessary fee.

FIG. 1A, schema for self-assembled vascular derivatives. (i) hPSCs are differentiated toward EVCs that can be matured into functional ECs and pericytes. (ii) Derived EVCs are embedded within a synthetic HA matrix that facilitates self-organization into vascular networks. FIG. 1B, VEcad expression in day 12 differentiated hiPSC-MR31 cell line and hESC-H9 cell line comparing the three tested differentiation conditions (flow cytometry analysis; n=3). FIG. 1C, flow cytometry plots (n=3) of EVC derivatives assessing expression of CD105, CD146, CD73 with VE-cad (hiPSC-MR31); FIGS. 1D-E, flow cytometry plots (n=3) of EVCs assessing expression of pluripotent markers Tra-1-60 and Tra-1-81, and hematopoietic marker CD45 (hiPSC-BC1). FIG. 1F, quantitative real time RT-PCR of H9-EVCs for the expression of SMMHC and peripherin compared to undifferentiated cells (d0) and mature derivatives (Lee et al., 2010; Wanjare et al., 2012). Isotype controls for flow cytometry are in gray. Flow cytometry results shown are typical of the independent experiments.

FIG. 2A, sorted VEcad+ from hiPSC-BC1- derived EVCs sub-cultured for an additional 6 days in SB431542-supplemented conditions and analyzed for the expression of VEcad, CD31 and CD146 (representative flow cytometry plots; n=3); FIG. 2B, sub-cultured sorted VEcad+ exhibited membrane localization of CD31 and VEcad (both in red), lectin binding (in green), cytoplasmic expression of eNOS, punctuated vWF, and uptake of AcLDL (in red). FIG. 2C, hiPSC-BC1-derived EVCs sub-cultured for an additional 6 days in pericyte-inducing conditions (Orlidge and D'Amore, 1987) were analyzed for the expression of NG2, CD73, PDFGRβ, CD44, CD146 and CD105 via flow cytometry. In FIG. 2D cells exhibited appropriate localization of PDGFRβ, NG2 and calponin (all in green) as demonstrated via immunofluorescence. Isotype controls for flow cytometry are in gray. Nuclei in blue. Results shown are typical of the independent experiment. Scale bars are 100 µm. FIG. 2E, quantitative real time RT-PCR of differentiating BC1 depicting expression of Notch1, Notch4, and Dll4 transcripts along differentiation. FIG. 2F, flow cytometry of VEcad expression along differentiation under DAFT-treated (orange) and control (red) conditions. FIG. 2E, quantitative real time RT-PCR demonstrating expression of VEcad and Id1 along the differentiation under DAFT-treated (red) and control (red) conditions.

FIG. 3A shows network formation from EVCs in (i) collagen and (ii) HA hydrogels. FIG. 3B shows sorted VEcad+ and VEcad− cells encapsulated within collagen gels were unable to form networks (VEcad− insert is an example of a cell with typical stellate morphology; phalloidin in green, nuclei in blue); scale bars are 100 µm. FIG. 3C shows that vacuole formation was observed after one day as evident by: (i) light microscopy (LM) and (ii) confocal images of vacuole vital stain, FM4-64, in red and nuclei in blue. Scale bar is 10 µm. FIG. 3D shows that on day 2, network formation with (i-ii) enlarged lumen and (iii-iv) cell sprouting were visualized by LM images (i and iii) and confocal images of FM4-64 in red and nuclei in blue (ii and iv). Scale bar in (i) and (iii) are 10 µm; in (ii) is 20 µm; and in (iv) is 50 µm. FIG. 3E shows that on day 3, complex networks were observed with enlarged and open lumen as indicated by confocal z-stacks and orthogonal sections of FM4-64 in red and nuclei in blue. Scale bar is 20 µm. FIG. 3F shows that after 3 days, multilayered structures were also detected as demonstrated by confocal 3D projection of NG2 (green), FM4-64 (red), and nuclei (blue) showing NG2+ pericyte (green) integrated with luminal structures. Images shown are typical of the independent experiment. Scale bar is 50 µm.

FIG. 4A shows that confocal images of two week explants of BC1-EVC networks in HA hydrogels demonstrate incorporation of human cells (red; arrows) into host vessels (green; arrows) and human cells exhibiting pericyte behavior (arrowhead). Scale bars are 50 µm. (i and ii: high mag of indicated regions) FIGS. 4B and 4C show histological examinations of the explants stained for CD31 expression via (FIG. 4B) immunofluorescence (CD31, red blood cells, and DAPI in red, green, and blue respectively; scale bar is 10 µm) and (FIG. 4C) immunohistochemistry (CD31 in brown, counterstain in blue; scale bar is 50 µm) reveal functional vessels containing human CD31+ cells with perfused blood cells. *perfused human vessel; # perfused mouse vessel FIG. 4D shows that quantification of cross-sectional areas and vessels per $mm^2$ of microvasculature containing human CD31+ cells depicts large perfused vessels and smaller non-perfused vessels in explants. FIG. 4E shows that immunofluorescence staining of sectioned explants for NG2+ (red) cells reveals functional human pericytes wrapping perfused vessels. Red blood cells in green, DAPI in blue. Scale bar is 10 µm.

FIG. 9a, hPSCs were differentiated in monolayer for 6 days followed by an additional 6 days in medium supplemented with and without SB431542 in low and high VEGF concentrations and analyzed using flow cytometry (n=3) for Tra-1-60 expression. Tra-1-60 expression was downregulated in all conditions examined. FIG. 9b, H9-EVCs differentiated in media supplemented with SB431542 and using high VEGF concentrations were analyzed for the expression of Tuj1 using quantitative real time RT-PCR compared to undifferentiated cells (d0) and mature derivatives (Lee et al., 2010). Significance levels were set at *p<0.05, p<0.01, and *p<0.001. Data are reported ±SEM.

(FIG. 11b) membrane localization of VEcad and CD31 (both in red), cytoplasmic expression of vWF and eNOS (both in green) and uptake of acLDL (in red). Nuclei are counterstained in blue.

FIG. 11c shows representative flow cytometry plots (n=3) of VEcad and CD31 expression in hiPSC-BC1- and hESC-H9-derived EVCs subcultured for an additional 6 days in SB431542-supplemented conditions. Isotype controls for flow cytometry are in gray. In FIG. 11d, sorted VEcad+ cells from EVCs of the different hPSC-lines were sub-cultured for an additional 6 days in SB431542-supplemented conditions and analyzed for the expression of ICAM1 in response to TNFα. Significance levels were set at *p<0.05, p<0.01, and *p<0.001. Data are reported ±SEM.

FIG. 13a, hiPSC-BC1-derived EVCs sub-cultured for an additional 6 days in pericyte-inducing conditions (Orlidge and D'Amore, 1987) were analyzed for the expression of CD31 and VEcad via flow cytometry (representative flow cytometry plots; n=3). Isotype controls for flow cytometry are in gray. Results shown are typical of the independent experiments. Derived pericytes differentiated into mesenchymal lineages including (FIG. 13b) adipocytes (Oil Red O stain) and (FIG. 13c) osteoblasts (Alizarin Red S stain). Scale bar is 50 μm.

FIG. 14a, EVC derivatives (hESC-H9) were encapsulated in collagen gels and cord-like structure formation was observed during the culture period. Scale bars are 100 μm.

FIGS. 15b-c, sprouting and initial network formation on day 2 as indicated by (FIG. 15b) LM (scale bar is 100 μm) and (FIG. 15c) serial confocal z-stack images of vacuole vital stain, FM4-64 (red) and nuclei (blue) (scale bar is 50 μm); and (FIG. 15d) complex networks on day 3 as indicated by (i) light microscopy (scale bar is 100 μm), with enlarged and open lumen as indicated by (ii) confocal z-stacks and orthogonal sections of vacuole vital stain, FM4-64 (red) and nuclei (blue). Images shown are typical of the independent experiments.

FIG. 16c, Flow cytometry analysis (n=3) confirms that EVCs cultured in HA hydrogel culture media for three days acquire NG2 expression. Images shown are typical of the independent experiment. Inset is isotype control. Scale bar is 20 μm.

FIG. 17c, Histological examination of BC1-MG explants after 1 week reveals functional microvasculature containing human CD31+ cells (brown; counterstain in blue) as indicated by blood cell perfusion. Scale bar is 50 μm.

FIG. 19a, Confocal images of two week explants of BC1-EVC networks in HA hydrogels reveals functional human NG2+ (green) pericytes proximal to host vessels (purple) in two week explants. Human cells are in red (PKH26). FIGS. 19b-c, Histological examination of in vivo explants of hESC-H9-EVC networks in HA hydrogels after two weeks also depict NG2+ pericytes wrapping perfused vessels via (FIG. 19b) immunofluorescence staining on cross sections of explants. Scale bar is 20 μm, and (FIG. 19c) immunohistochemistry for NG2 (in brown; an example is indicated by arrow). Scale bar is 10 μm.

DETAILED DESCRIPTION OF THE INVENTION

The following description is provided to enable any person skilled in the art to make and use the invention and sets forth the best modes contemplated by the inventor of carrying out his invention. Various modifications, however, will remain readily apparent to those skilled in the art, since the general principles of the present invention have been defined herein specifically to provide a method for causing pluripotent stem cells to differentiate into functional vascular networks.

Derivation of EVCs from hPSCs

Figure 5:
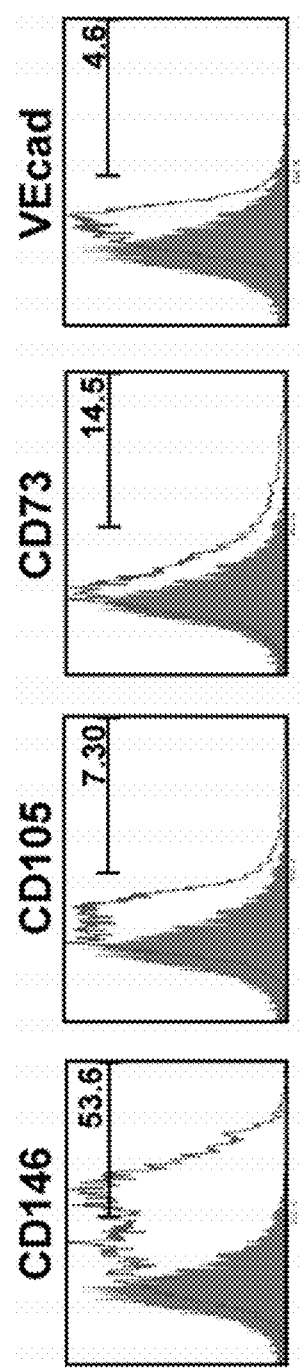
FIG. 5 shows differentiating hPSCs. hiPSC-BC1 were differentiated in monolayer for 6 days and analyzed using flow cytometry analysis (n=3) for markers of interest including CD146, CD105, CD73 and VEcad. Isotype controls for flow cytometry are in gray. Results shown are for hiPSC-BC1 cell line and typical of the independent experiments.
Figure 6:
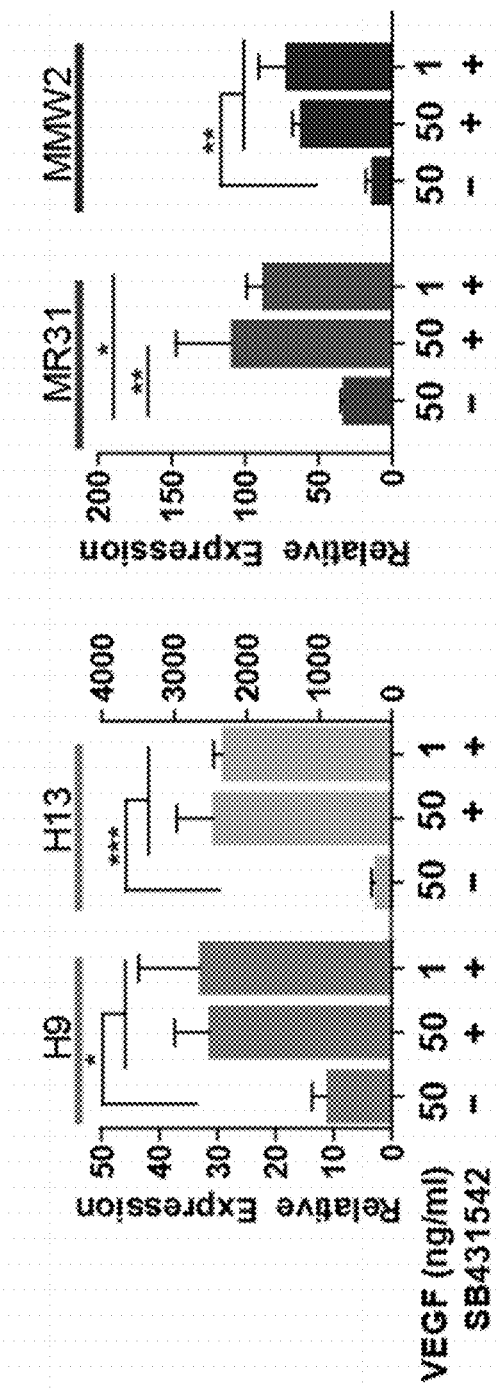
FIG. 6 shows the effect of VEGF and TGFδ inhibitor on VEcad expression. hPSCs were differentiated in monolayer for 6 days followed by an additional 6 days in medium supplemented with and without SB431542 in low and high VEGF concentrations and analyzed using real-time PCR for VEcad expression (n=3). VEcad expression was upregulated with the addition of TGFβ inhibitor independently of VEGF concentrations in all hPSC lines tested. Significance levels were set at *p<0.05, p<0.01, and *p<0.001. Data are reported ±SEM.

Toward clinically relevant outcomes and because microvascular architecture is a bicellular entity, we first sought to develop a robust and controlled method to differentiate hPSCs into a bicellular population with maturation capacity to both ECs and pericytes. Vascular endothelial cadherin (VEcad) expression has been shown to specify lineage commitment of ECs (James et al., 2010), while CD105, CD146, and CD73 have been proposed to mark pericyte progenitors (Dar et al., 2011) though also expressed in mature ECs (Airas et al., 1995; Bardin et al., 2001; Duff et al., 2003). Acknowledging that co-cultures of pericytes and ECs typically result in pericyte-mediated EC growth inhibition (Dar et al., 2011; Orlidge and D'Amore, 1987), we focused on inducing VEcad+ cells early on in the differentiation scheme to ensure EC maturation. Using a step-wise differentiation procedure, hPSCs (listed in Table 1) were first allowed to undergo differentiation in monolayer (as seen in FIG. 5). The subsequent addition of transforming growth factor β inhibitor, SB431542 (James et al., 2010), supplemented with either high (50 ng/ml) or low (1 ng/ml) vascular endothelial growth factor-A (VEGF-A) concentrations yielded upregulation of VEcad expression, ranging from 20-70% VEcad+ cells (see FIG. 1b and FIG. 6) depending on hPSC cell line. The expression levels of CD31 were not altered at the different conditions while VEGF receptor-2

Figure 1:
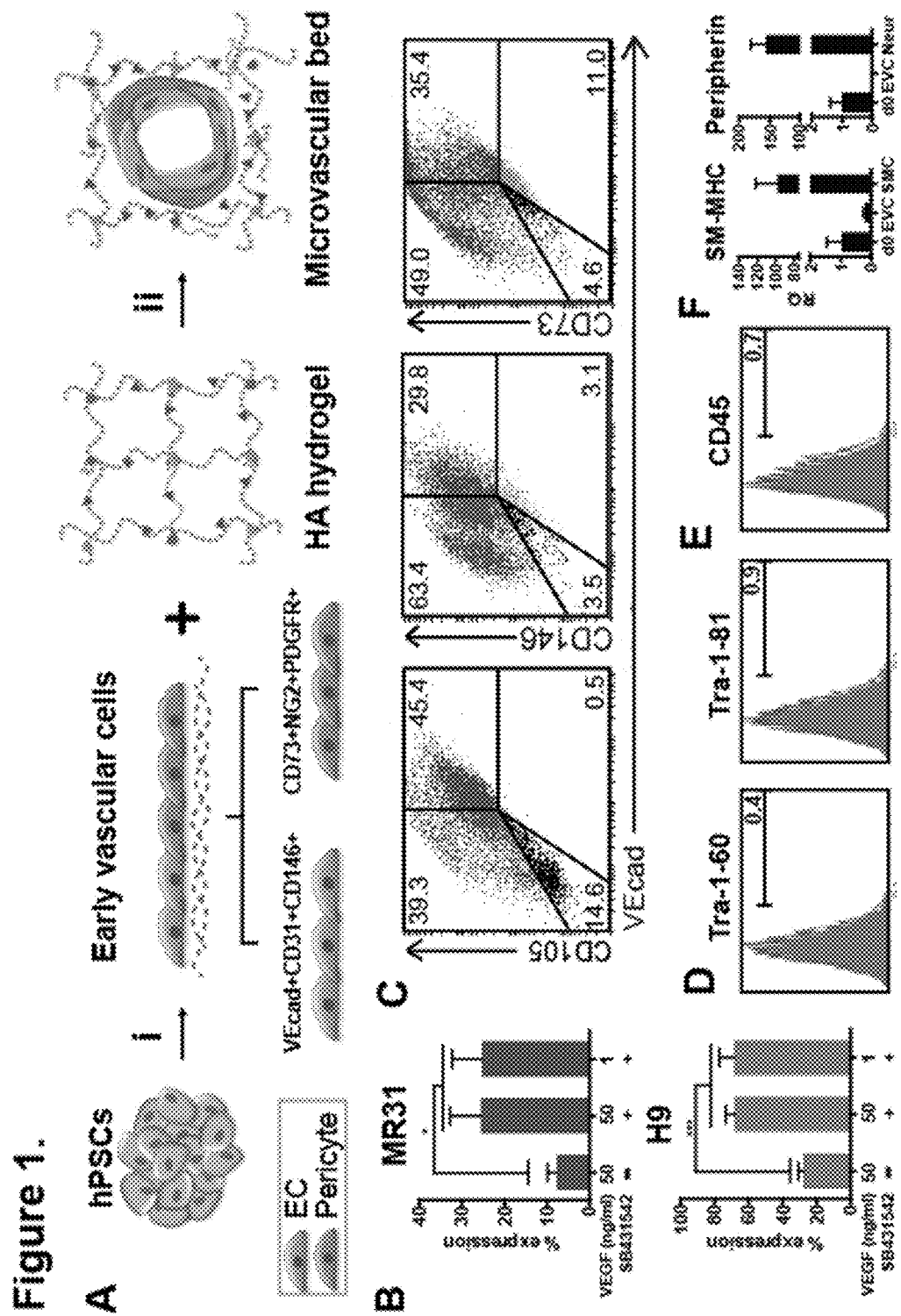
FIG. 1 shows derivation of EVCs from hPSCs.
Figure 7:
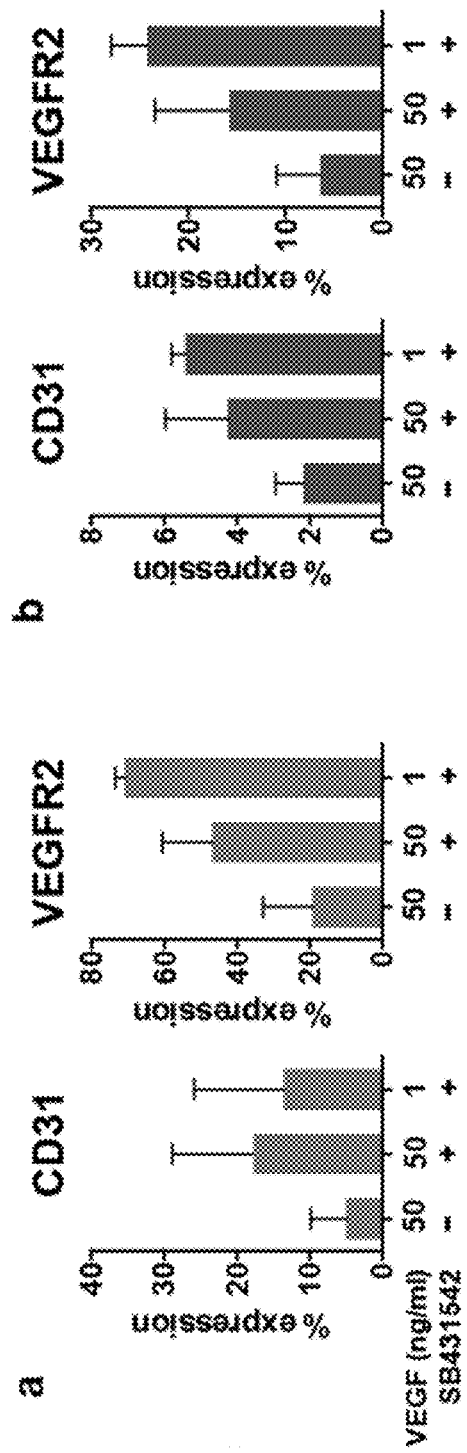
FIG. 7 shows the effect of VEGF and TGFβ inhibitor on CD31 and VEGFR2 expression. hPSCs were differentiated in monolayer for 6 days followed by an additional 6 days in medium supplemented with and without SB431542 in low and high VEGF concentrations and analyzed using flow cytometry (n=3) for CD31 and VEGFR2 expression in (a) hESC-H9 and (b) hiPSC-MR31 lines. CD31 expression did not change in the different treatments, while VEGFR2 expression was upregulated in media supplemented with low VEGF concentration. Data are reported ±SEM.
Figure 8:
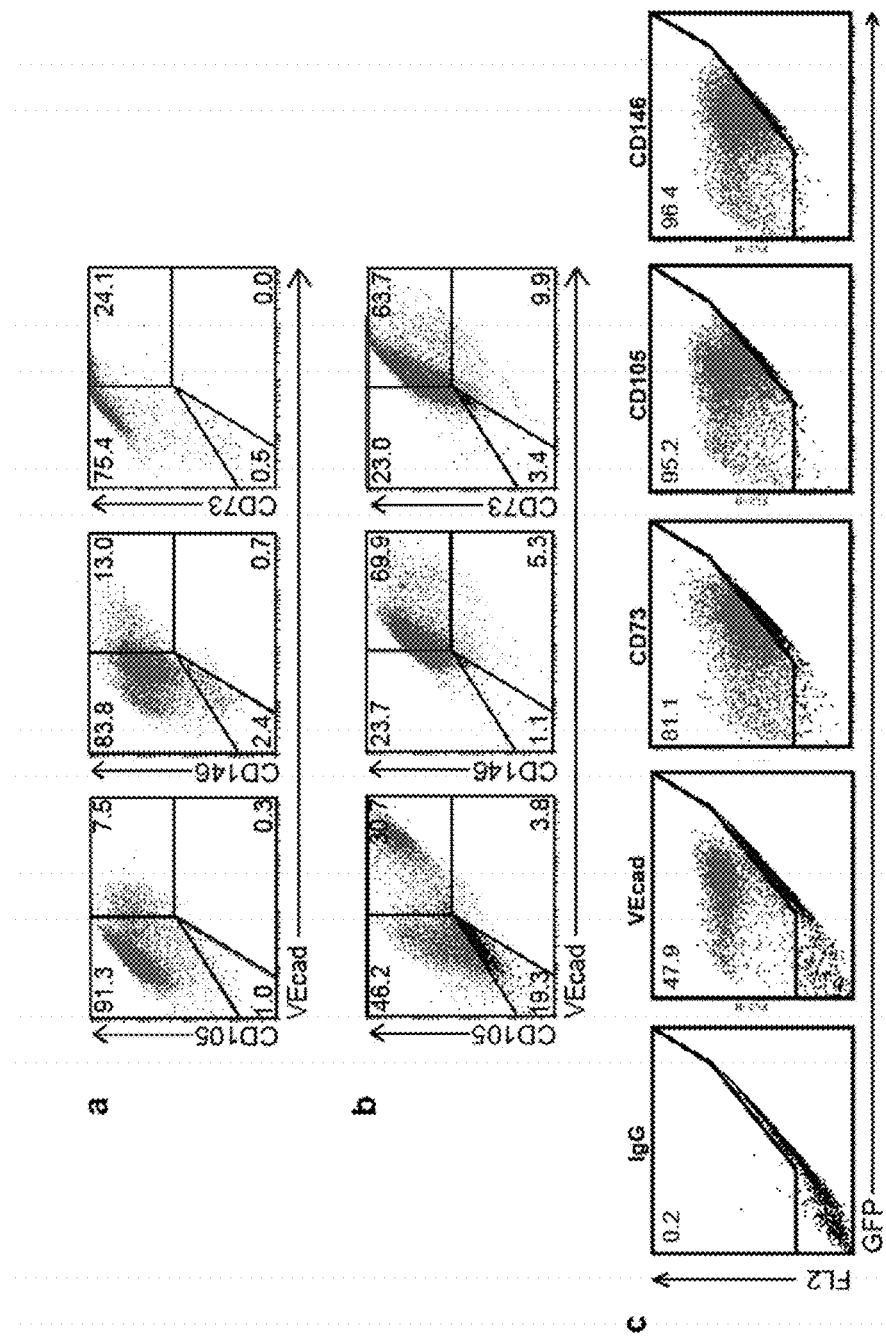
FIG. 8 shows marker expression in EVCs. hPSCs were differentiated in monolayer for 12 days and EVC derivatives were analyzed using flow cytometry (n=3) assessing co-expression of CD105, CD146, CD73 with VE-cad from (a) hESC-H9 and (b) hiPSC-BC1 differentiated cells. (c) EVCs were also derived from a GFP transgenic hiPSC line (Haase et al., 2009) and confirmed for their marker expression profile by flow cytometry. Results shown are typical of the independent experiments.
Figure 9:
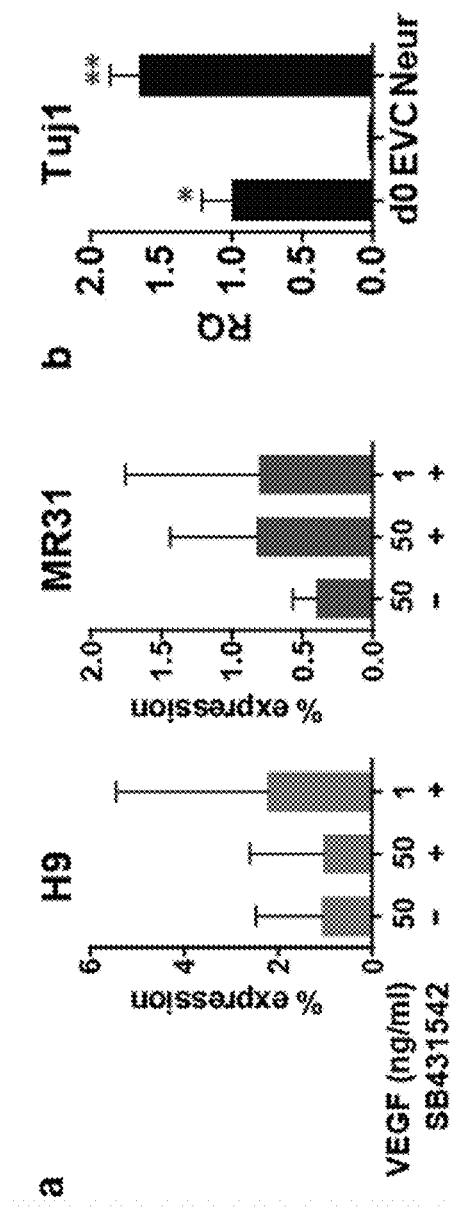
FIG. 9 shows pluripotent and neuronal marker expression in EVCs.
Figure 10:
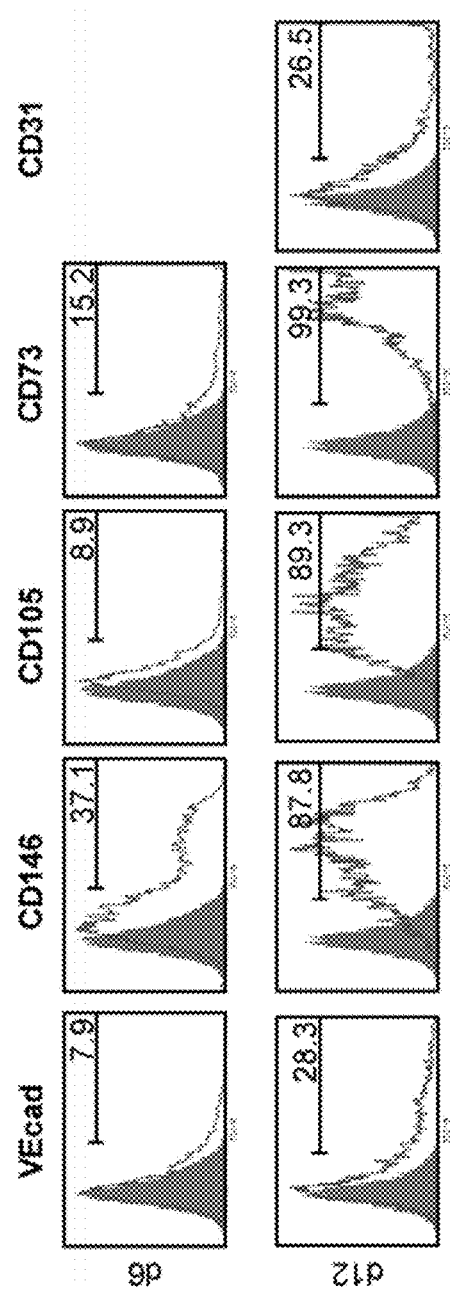
FIG. 10 shows EVCs derived using serum-free conditions. Flow cytometry (n=3) analysis of hiPSC-BC1-derivatives after 6 and 12 days of differentiation in serum-free conditions reveals marker expressions comparable to that of the standard differentiation scheme. Results shown are typical of the independent experiments.

(VEGFR2/KDR) expression was higher in media supplemented with a low VEGF concentration (shown in FIG. 7). Greater than 95% of this cell population was positive for CD105 and CD146 in all cell lines examined, and about 80% of the cells expressed CD73 (see FIG. 1c and FIG. 8). Expression of Tra-1-60 and Tra-1-81, markers of pluripotency, was <1% when using high VEGF concentrations, indicating the vast majority of cells had been differentiated (see FIG. 1d and FIG. 9a). Thus, EVCs were differentiated in media supplemented with SB431542 and using high VEGF concentrations. EVCs were negative for hematopoietic marker CD45 (FIG. 1e), and demonstrated negligible expression of smooth muscle cell marker, smooth muscle myosin heavy chain (SMMHC), as well as peripheral neuron markers, peripherin and Tuj1 (FIG. 1f and FIG. 9b). Comparable marker expression profiles were obtained from EVCs derived using serum free conditions in our adherent differentiation scheme (see FIG. 10). From these analyses, we considered this derived population to be vascular lineage specific.

TABLE 1

| hPSC line | Type | Reprogramming factors | Source | Ref. |
|---|---|---|---|---|
| H9 | hESC | — | blastocyst | (Thomson, 1998) |
| H13 | hESC | — | blastocyst | (Thomson, 1998) |
| MR31 | hiPSC | OSK | IMR90 (normal, fetal lung fibroblasts, XX) | (Mali et al., 2010) |
| MMW2 | hiPSC | OSKM | MSC1640 (normal MSCs from 24 y/o, XY) | (Zou et al., 2011) |
| BC1 | hiPSC | Plasmid encoding OSKML | CD34+ cells from bone marrow | (Cheng et al., 2012; Chou et al., 2011) |
| GFP-hiPSC | hiPSC | OSLN | Cord blood-derived ECs | (Haase et al., 2009) |

O = OCT4;
S = SOX2;
K = KLF4;
M = c-MYC;
L = LIN28;
N = NANOG

Differentiation Protocol.

Human PSCs were collected through digestion with ethylenediaminetetraacetic acid (EDTA; Promega), separated into an individual cell suspension using a 40-μm mesh strainer (BD Biosciences) and plated onto collagen IV (Trevigen) coated plates at a concentration of $5 \times 10^4$ cells/cm$^2$. Cells were cultured for 6 days in a differentiation medium composed of alpha-MEM (Invitrogen), 10% FBS (Hyclone) and 0.1 mM β-mercaptoethanol (β-ME), with the media changed daily. On day 6, differentiated cells were collected through digestion with TrypLE (Invitrogen), separated with a 40-μm mesh strainer, and seeded at a concentration of $1.25 \times 10^4$ cells/cm$^2$ on collagen-type-IV-coated plates in endothelial cell growth media (ECGM) (PromoCell) supplemented with 2% FBS, 50 ng/ml VEGF with or without TGF-β (10 μM SB431542 (Tocris)), or 1 ng/ml VEGF+10 μM SB431542 for 6 days. Media was changed every other day. For Notch studies, differentiating cells were treated with gamma secretase inhibitor, DAPT (10 μM; Sigma) for the second 6 days of differentiation. To elucidate whether serum-free conditions could be used to derive EVCs, we followed the aforementioned protocol except differentiating the cells in alpha-MEM media supplemented with 20% knockout serum replacement, 0.1 mM β-ME, 1× non-essential amino acids (Gibco), and 1× L-glutamine (Invitrogen) for 6 days, followed by 6 days in ECGM base media (Promocell) supplemented with 50 ng/ml VEGF, 10 μM SB431542, 10% knockout serum replacement, β-ME, essential amino acids, and glutamine. For this process the plates can be coated with a variety of suitable materials which include type I collagen and fibronectin as well as type IV collagen. SB431542 is a convenient TGF-β inhibitor for this process. Other TGF-β inhibitors or siRNA inhibition of TGF-β are also operational.

Maturation of EVCs: ECs

Figure 2:
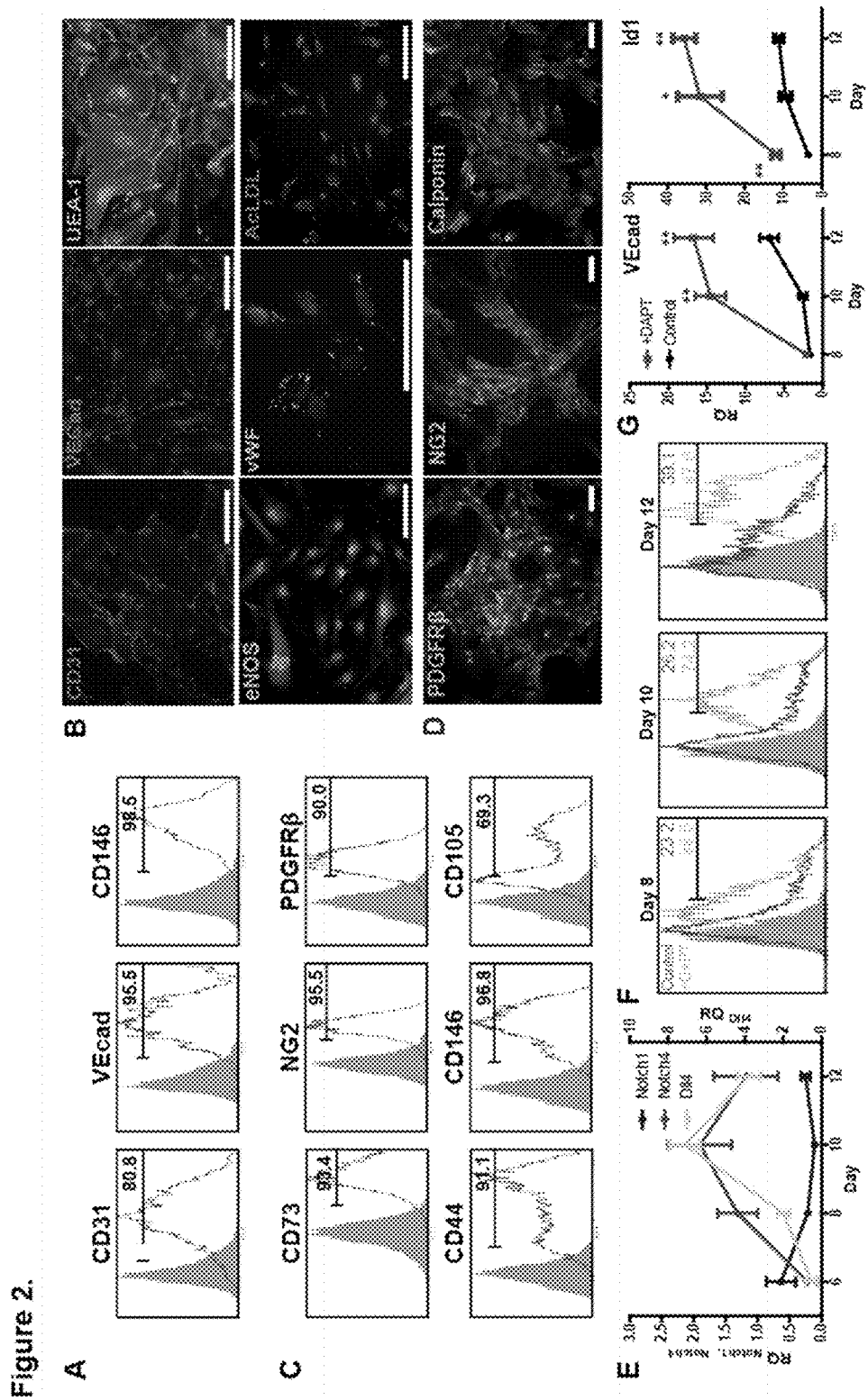
FIG. 2 shows EVC maturation and Notch signaling involvement.
Figure 11:
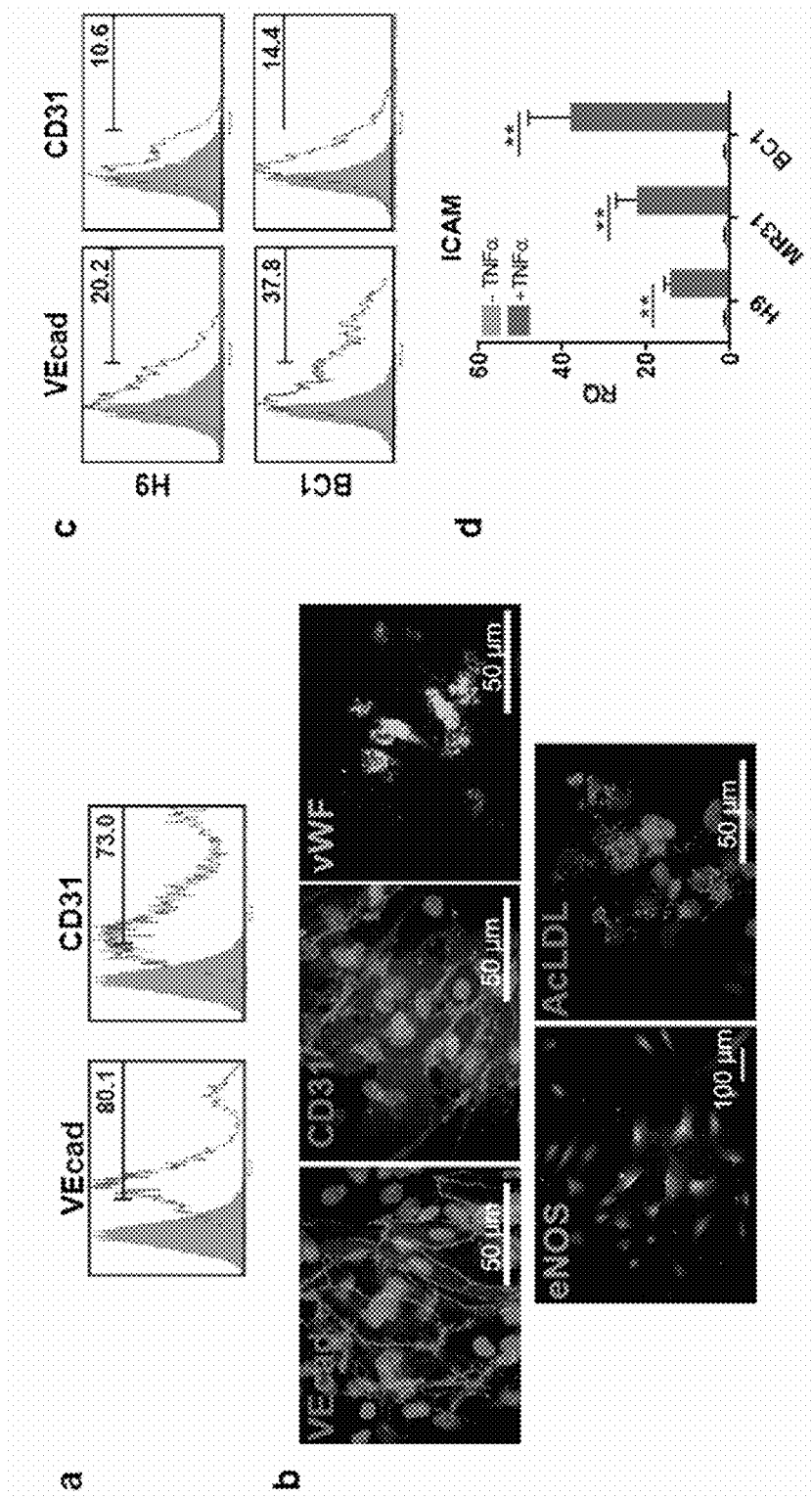
FIG. 11 shows EC maturation. hiPSC-MR31-derived EVCs were sub-cultured for an additional 6 days in SB431542-supplemented conditions and analyzed for (FIG. 11a) the expression of VEcad and CD31 expression (representative flow cytometry plots; n=3)
Figure 12:
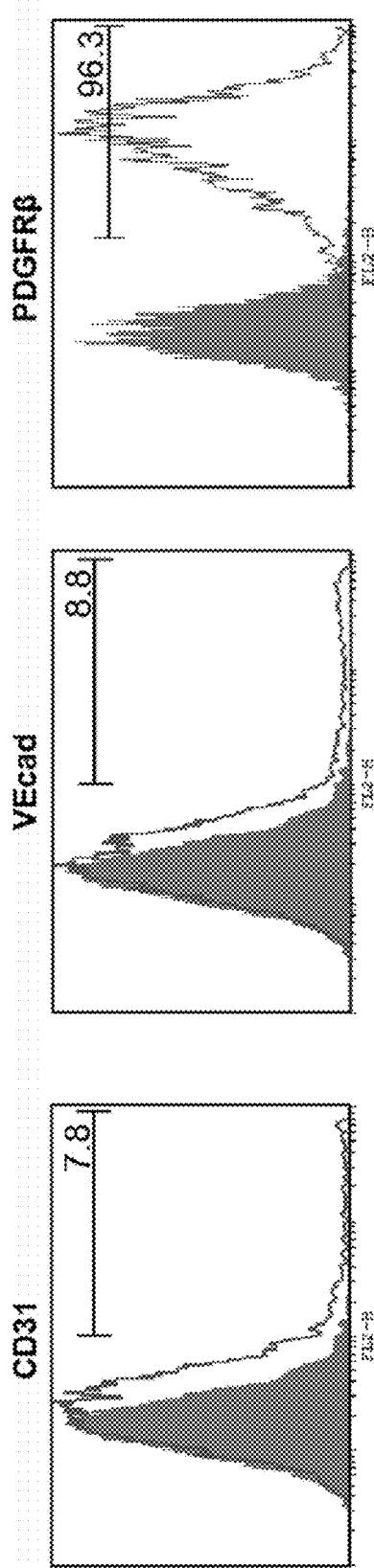
FIG. 12. shows sorted VEcad– cells. Sorted VEcad– cells from hiPSC-BC1-derived EVCs sub-cultured for an additional 6 days in SB431542-supplemented conditions and analyzed for the expression of VEcad, CD31, and PDGFRβ (representative flow cytometry plots; n=3). Isotype controls for flow cytometry are in gray. Results shown are typical of the independent experiments.

To examine the endothelial potential of hPSC-EVCs, two approaches were examined: we either sub-cultured EVCs or sorted and expanded VEcad+ cells, both under the same culture conditions (i.e., 50 ng/ml VEGF and SB431542). Sub-culturing yielded ECs that were enriched in VEcad and CD31 (FIGS. 11a, b); however, this approach and enrichment without cell sorting varied among three different hPSC lines; a hiPSC line with vector integration gave rise to the best result as seen in FIG. 11c. Sorted VEcad+ cells from EVCs matured toward VEcad+CD31+CD146+ECs as shown in FIG. 2a. The cells exhibited typical membrane expression of VEcad and CD31, lectin binding, cytoplasmic expression of endothelial nitric oxide synthase (eNOS) and von Willebrand factor (vWF), uptake of acetylated low density lipoprotein (AcLDL), and upregulation of intercellular adhesion molecule 1 (ICAM1) in response to tumor necrosis factor α (FIG. 2b and FIG. 11d). Sorted VEcad– cells could not mature to ECs and acquired expression of PDGFRβ (FIG. 12). These data were consistent among the different hPSC lines examined.

Maturation of EVCs: Pericytes

Figure 13:
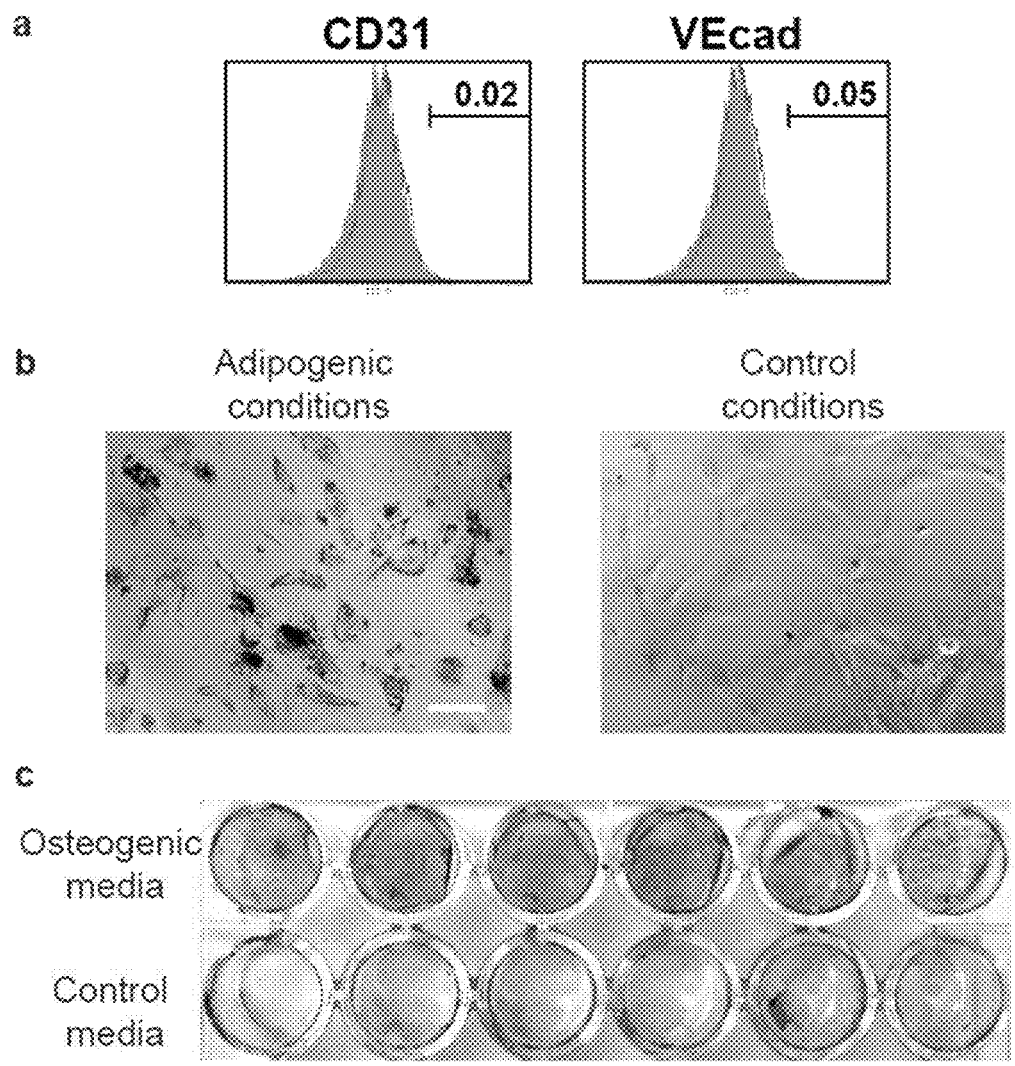
FIG. 13 shows pericyte maturation and mesenchymal differentiation potential.
Figure 14:
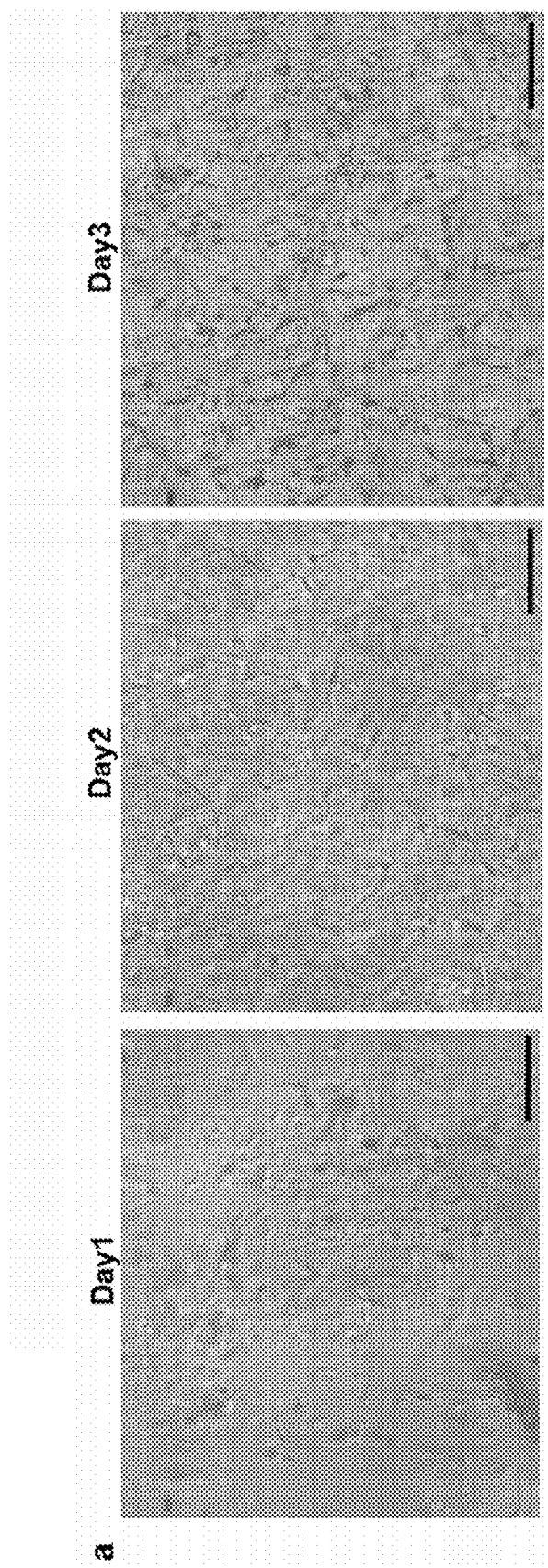
FIG. 14 shows cord formation by EVCs in collagen gels.

We next probed the pericyte potential of the EVCs by culturing them under pericyte-maturing conditions (Orlidge and D'Amore, 1987). The EVCs were cultured on a suitable surface (unattached cells were removed after 4 hours). The medium contained 10% serum although lower serum levels with Angiopoietin 1 or TGFb-1 are also effective. After 6 days of culture, the cells were enriched in pericyte markers CD73, NG2, platelet-derived growth factor β (PDGFRβ), and CD44 (Crisan et al., 2012) and depleted in EC markers VEcad and CD31 (FIG. 2c and FIG. 13a). Interestingly, most cells remained CD146+, but some cells lost CD105 expression (FIG. 2c). The spindle-shaped pericyte derivatives expressed PDGFRβ and NG2 proteoglycan and exhibited filamentous calponin expression (FIG. 2d), as expected for pericytes derived from fetal and adult sources. An important functionality of pericytes is their ability to behave as mesenchymal precursors (Crisan et al., 2008; Dar et al., 2011). Indeed, the pericyte derivatives in our culture could be differentiated to adipocytes and osteoblasts (see FIGS. 13b and 13c), demonstrating their mesenchymal potential. Taken together, the cellular analyses demonstrate that EVCs, which are CD105+CD146+ enriched for CD73 and VEcad contain the cellular makeup imperative to construct a functional microvasculature.

Putative Role of Notch Signaling

Previous studies have demonstrated that Notch cell-cell signaling is imperative for blood vessel development and stability (Hofmann and Iruela-Arispe, 2007; Sainson and Harris, 2008). Specifically, Notch4 and Notch ligand, Delta-like ligand 4 (Dll4), are particularly restricted to the vascular lineage with critical importance on heterotypic signaling between pericytes and ECs. To determine whether Notch signaling promotes co-differentiation toward a bicellular population, we monitored the expression of Notch receptors, Notch1 and Notch4, over the course of differentiation. We found that Notch4 expression increased over the differentiation, whereas Notch1 expression remained stagnant (FIG. 2e). Based on these findings, we also assayed for Dll4, which followed a similar trend to Notch4 expression (FIG. 2e). Using γ-secretase inhibitor, N-[N-(3,5-difluorophenacetyl)-L-alanyl]-S-phenylglycine t-butyl ester (DAPT), to inhibit Notch signaling yielded enrichment in VEcad+ cells compared to control conditions (FIG. 2f), with upregulation of both VEcad and Id1 transcripts under DAPT treatment (FIG. 2g). Notch signaling has been demonstrated to block EC proliferation. Thus we speculate inhibition of Notch may be impeding heterotypic cell signaling and promoting the proliferation of derived ECs through the differentiation period. Furthermore, inhibition of Notch signaling via the Dll4 receptor has been demonstrated to inhibit the potential of stem cells to mature toward pericytes (Stewart et al., 2011). Overall, our data supports numerous in vitro and in vivo studies suggesting the importance of Notch4 and Dll4 in vascular development (Sainson and Harris, 2008).

Self-Organization of Bicellular Vascular Networks in Hydrogels

Figure 3:
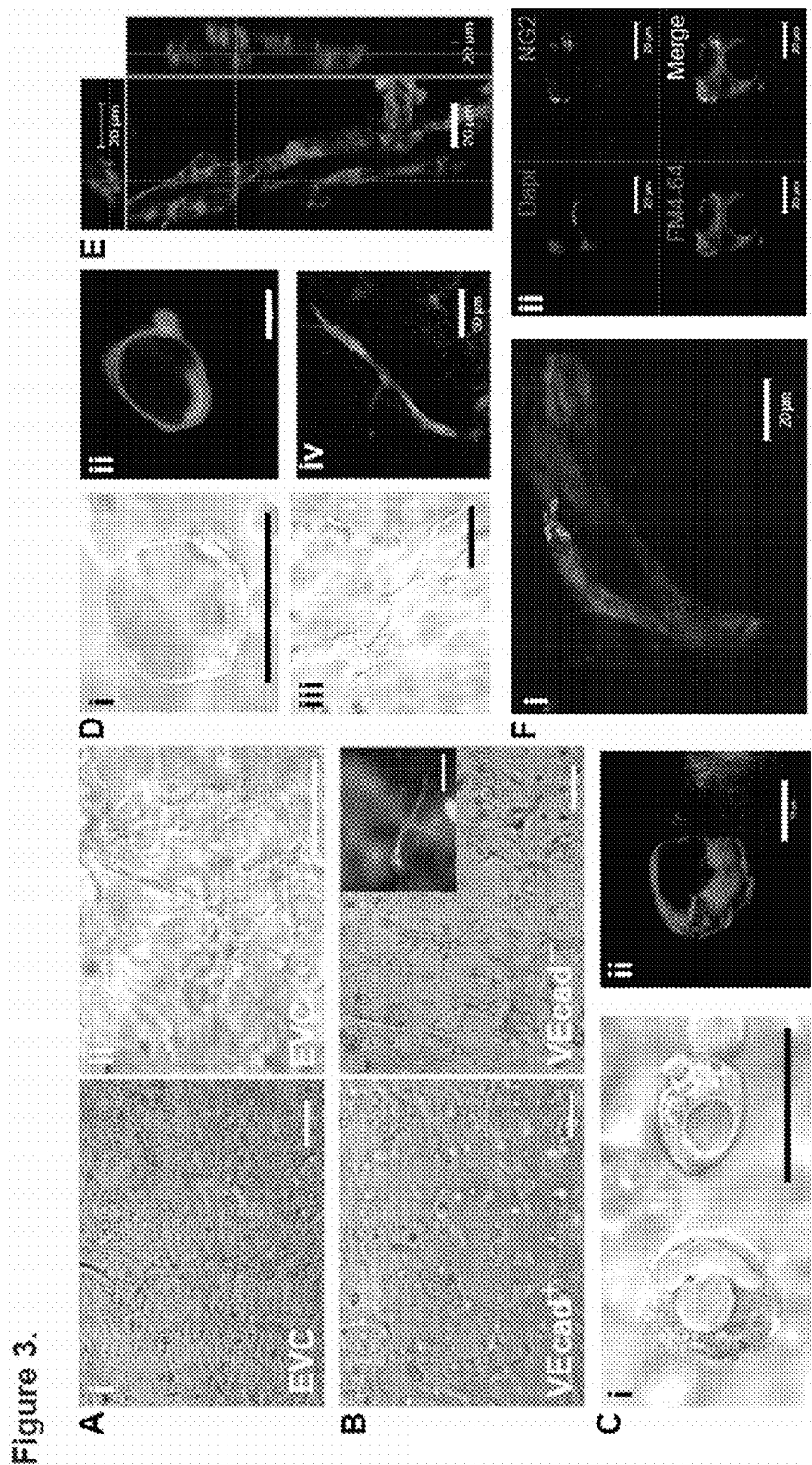
FIG. 3 shows self-assembly of EVCs to multicellular networks in three dimensional matrix.

To examine whether EVCs exhibit self-organizing capability into a bicellular microvascular bed, we tested network formation in collagen (Stratman et al., 2009a; Stratman et al., 2009b) and in completely synthetic hyaluronic acid (HA)-based hydrogel (Hanjaya-Putra et al., 2011) (FIG. 3A). We reasoned that derived EVCs would be able to work synergistically to form stable vascular networks in a three-dimensional matrix. Indeed, in both hydrogel systems, EVCs were found to form lavish networks (FIG. 3A); sorted VEcad+ or VEcad− cells were individually unable to form such networks when encapsulated within collagen gels (FIG. 3B). VEcad+ cells primarily formed vacuoles with some instances of sprouting (average circularity of 0.70±0.15 versus 0.36±0.23 for EVCs; FIG. 3B). VEcad-cells exhibited cell spreading and a characteristic stellate morphology, but no network formation.

Vascular Morphogenesis of EVCs within HA Hydrogels

Figure 15:
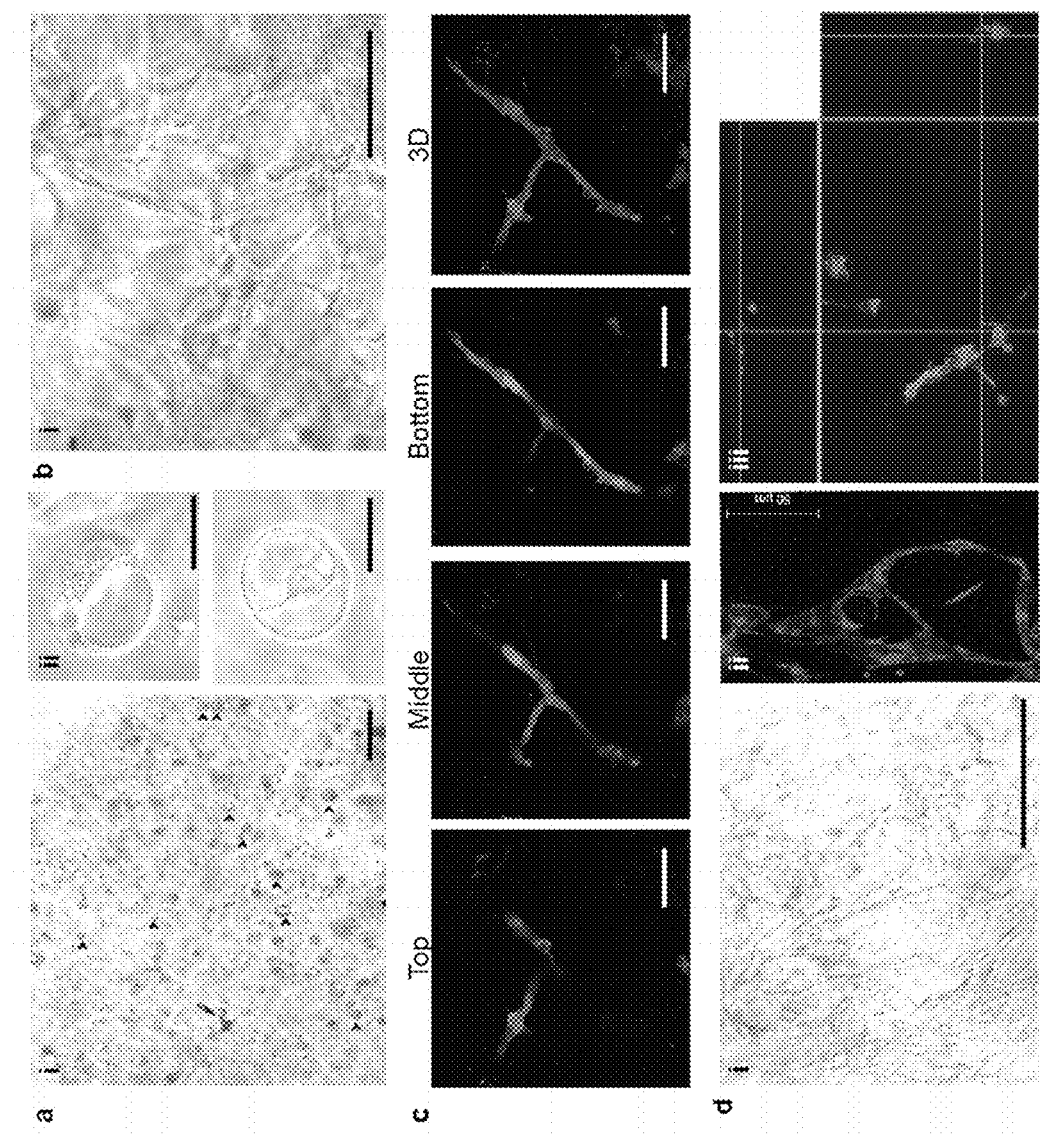
FIG. 15 shows network formation of EVCs in HA matrix. BC1-EVCs were encapsulated in HA hydrogels and the kinetics of network formation was documented along the culture period with (FIG. 15a) vacuole formation on day 1 as indicated by light microscopy (LM) images showing (i) low magnification (scale bar=100 μm; some vacuole are indicated by arrowheads) and (ii) high magnification of individual cells (scale bar is 5 μm)
Figure 16:
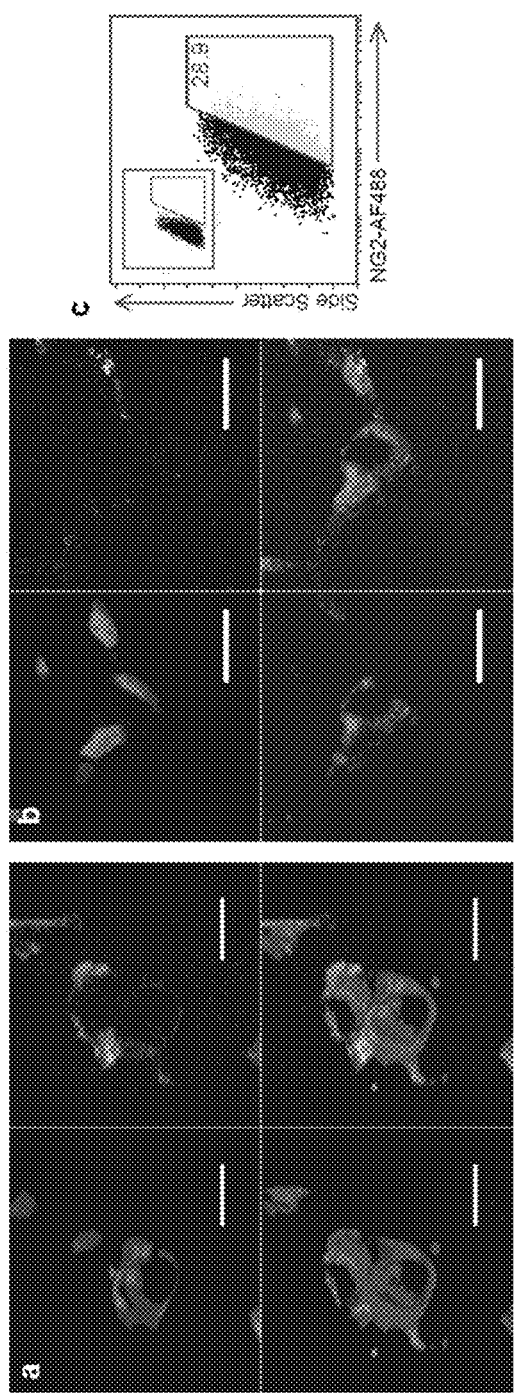
FIG. 16 shows derived pericytes in the vascular networks. EVCs were encapsulated in HA hydrogels and after three days in culture, multilayer structures were detected as demonstrated by confocal microscopy of NG2 (green), vacuole vital stain FM4-64 (red), and nuclei (blue) showing (FIG. 16a) pericytes integrated onto a hollow tubular structure (three dimensional projection) and (FIG. 16b) enclosing a luminal structure (confocal z-stack).

We next examined the mechanism by which EVC networks were formed within the HA hydrogel, a xeno-free, synthetic, construct engineered to recapitulate tubulogenesis-inducing signals (Hanjaya-Putra et al., 2011). In vitro assessment of cellular behavior revealed the formation of multicellular networks via a sequential process typical of vascular morphogenesis. After one day of culture, we observed vacuole formation in many, but not all, of the cells. Some of these vacuoles had coalesced into a larger structure, resembling lumen (FIG. 3A and FIG. 15a). After two days of culture, we could observe the progression of tubulogenesis including extensive sprouting and occasions of open lumen (FIG. 3b and FIG. 15b). By day 3, vascular networks grew; we clearly observed comprehensive multicellular networks within HA hydrogels. Complex vascular networks with patent lumen structures were easily detected throughout the hydrogels, suggesting a mature vascular network (FIG. 3C and FIG. 15c). Interestingly, on day 3 we could also observe instances of NG2+ pericytes incorporated in the luminal structures and encircling the forming tubular structures (FIG. 3D and FIG. 12).

Functionality of hPSC-Bicellular Vascular Constructs

Figure 4:
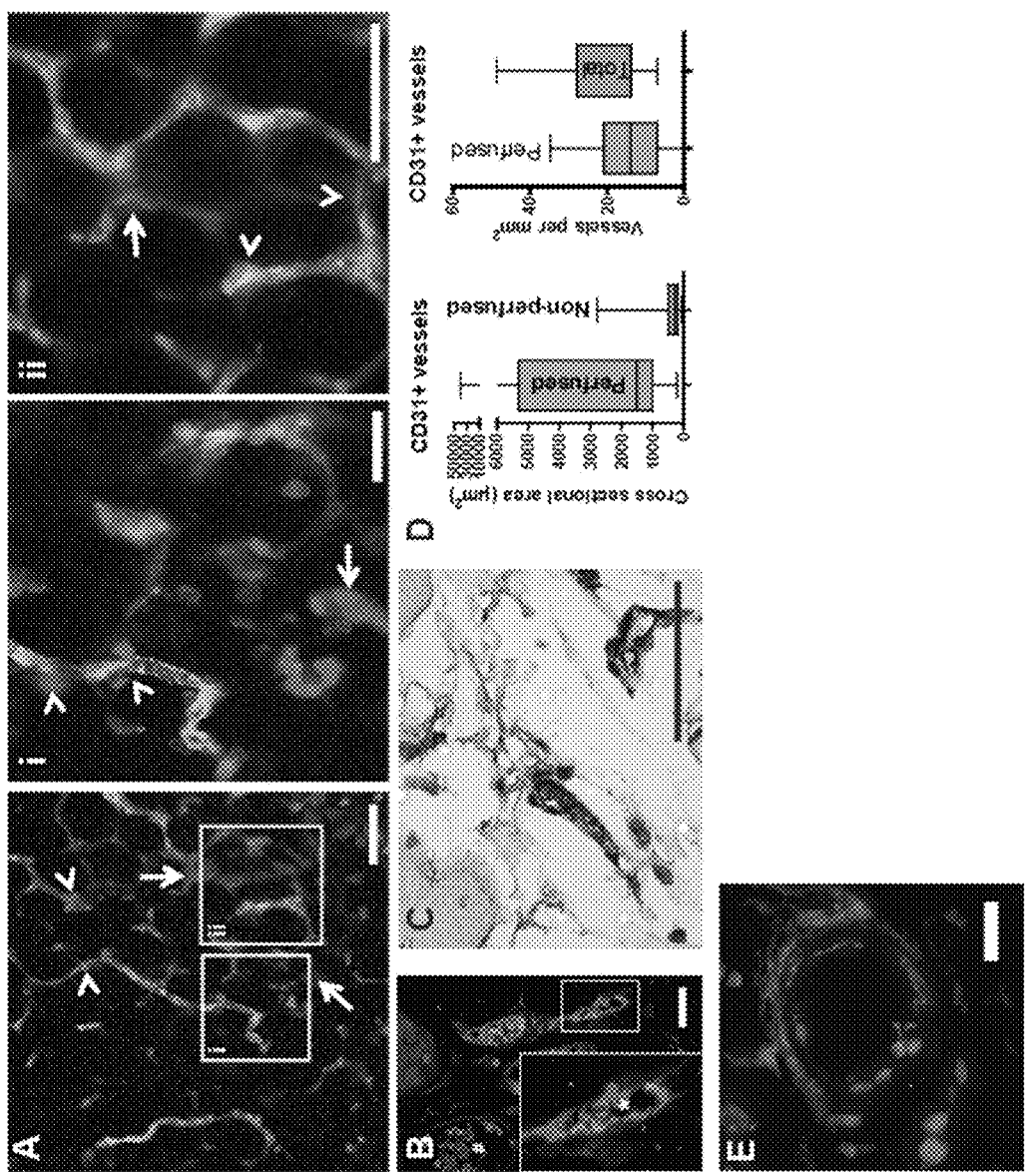
FIG. 4 shows perfusion of EVC networks in vivo in synthetic hydrogels.
Figure 17:
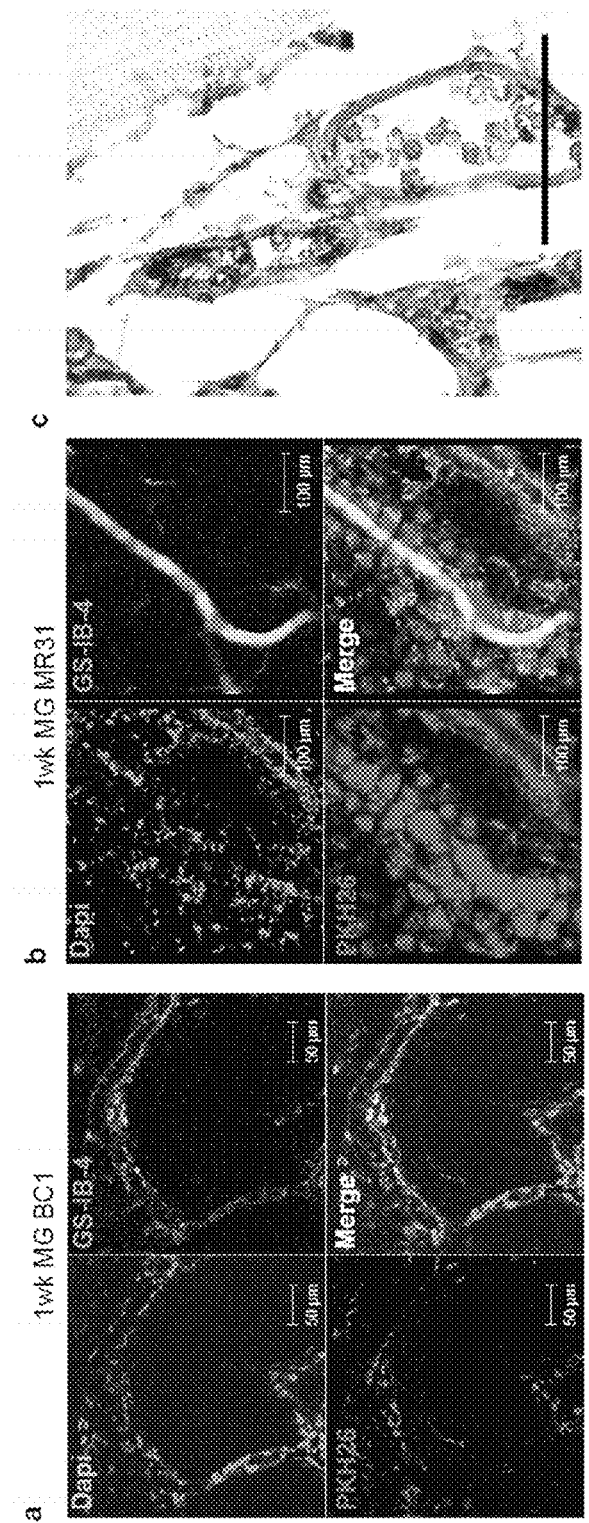
FIG. 17 shows in vivo functionality of EVCs. EVCs derived from (FIG. 17a) BC1 and (FIG. 17b) MR31 were dyed with PKH-26, implanted subcutaneously in Matrigel (MG) plugs and explants were analyzed after one week. Representative confocal z-stack images of perfused explants with fluorescein-conjugated GS-IB-4 lectin (green) show that EVCs integrated into host vasculature after one week (human cells in red). Some human vessels were not perfused (asterisk). Nuclei in blue.
Figure 18:
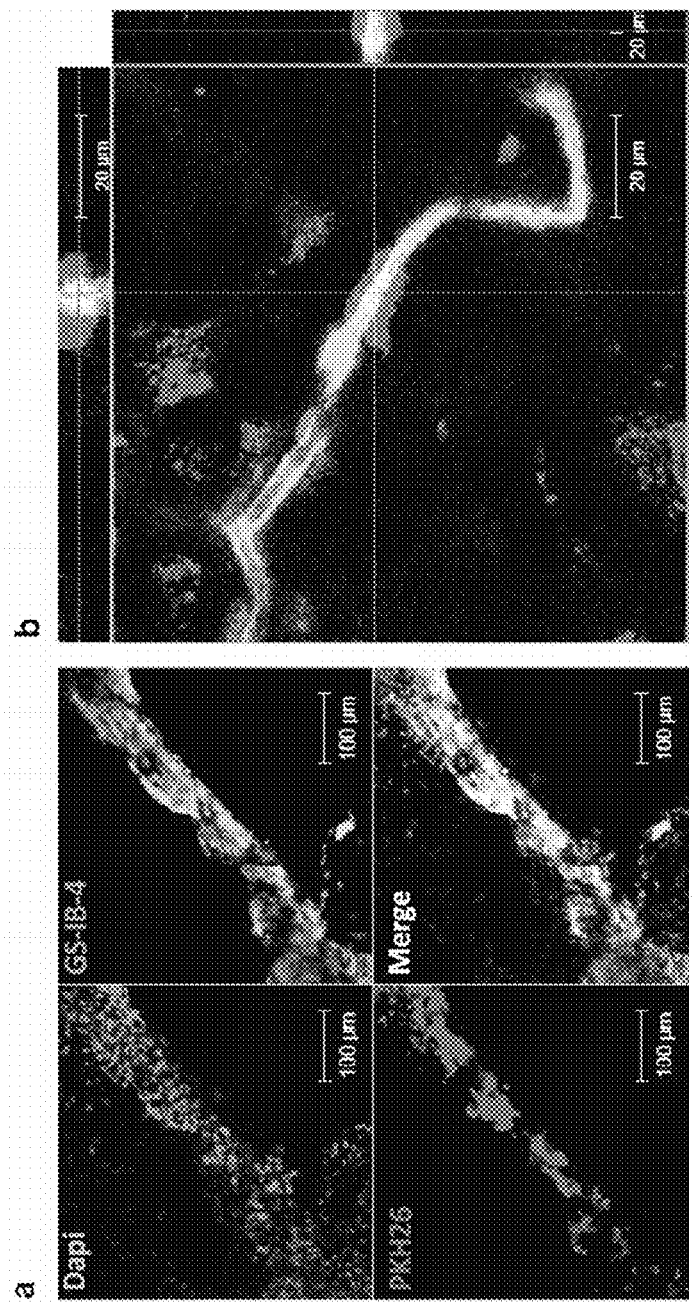
FIG. 18 shows EC and pericyte phenotypes in in vivo explants of BC1-EVC HA constructs. EVCs derived from BC1 were dyed with PKH-26, encapsulated in HA hydrogels, and cultured for 3 days, after which were implanted subcutaneously. Confocal z-stack images of two week explants perfused with fluorescein-conjugated GS-IB-4 lectin (green) showing human cells (red) interacting with the host vessels (green) via (FIG. 18a) incorporation into and (FIG. 18b) wrapping around penetrating host vessels.
Figure 19:
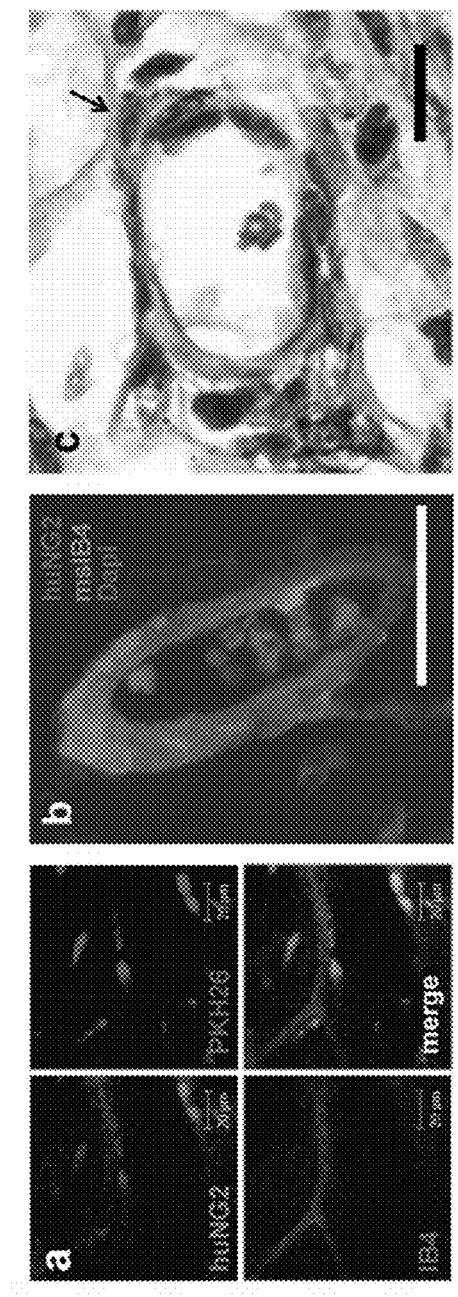
FIG. 19 shows derived pericytes in vivo.

In vivo functionality is crucial to the success of derived EVCs for regenerative medicine endeavors. We first tested whether EVCs will survive implantation, assemble into vascular networks, integrate with the host vasculature, and establish blood flow. Using a Matrigel plug assay (Ferreira et al., 2007), human EVCs incorporated with perfused host microvasculature, as well as generated human-only microvascular structures (see FIG. 17). To harness the self-organizing capability of EVCs in HA hydrogels, we subcutaneously implanted the engineered vascular networks and assessed their functionality. Human cells were found to incorporate into or wrap around the mouse microvasculature (FIG. 4A and FIG. 18). Perfused microvasculatures containing human ECs (with cross-sectional areas ranging from 100 to 25,000 $\mu m^2$) were abundant throughout the explant (~15 vessels per $mm^2$), demonstrating that the transplanted human vascular networks were functional and had anastomosed with the hosts' circulatory systems (FIGS. 4B-D). Moreover, NG2+ human pericytes were found to migrate towards and encircle the perfused vasculature (FIG. 4E and FIG. 19).

Experimental Procedures:

hPSC Culture. Human ESC lines H9 and H13 (passages 15 to 40; WiCell Research Institute, Madison, Wis.) and hiPSC lines MR31 (Mali et al., 2010), MMW2 (Zou et al., 2011), BC1 (Cheng et al., 2012; Chou et al., 2011), and a GFP transgenic hiPSC line (Clone 26 hCBiPS aMHC-neoPGKhygro+pCAGGS2 Passage 47+10, kindly provided by Dr. Ulrich Martin, Hannover Medical School, Germany) (Haase et al., 2009) were cultured as previously described (Vo et al., 2010; Wanjare et al., 2012). Cell lines were routinely examined for pluripotent markers using immunofluorescence staining and flow cytometry analysis for TRA-1-60, TRA-1-81, SSEA4, and Oct4. See Table 1 (above) for details on the various hPSCs.

Flow Cytometry. Flow cytometry was performed as previously described (Kusuma et al., 2012). Briefly, cells were incubated with FITC- or PE-conjugated antigen specific antibodies for markers (see Table 2 for antibody types and sources). All analyses were done using corresponding isotype controls. Forward versus side light scatter plots were used to exclude dead cells. User guide instructions were followed to complete the flow cytometry analysis via Cyflogic v1.2 software.

TABLE 2

| Antibody | Source | Catalog # | Purpose | Host Species & Reactivity | Concentration |
| --- | --- | --- | --- | --- | --- |
| AcLDL | Invitrogen | L-3484 | IF | ECs | 10 µg/ml |
| Alexa Fluor 488 | Invitrogen | A11008 | IF | Goat anti-rabbit | 1:1,000 |
| Calponin | Dako | M3556 | IF | Mouse anti-human | 1:100 |
| CD105-PE | eBioscience | 12-1057-41 | FC | Mouse anti-human | 1:10 |
| CD146-PE | BD | 550315 | FC | Mouse anti-human | 1:10 |
| CD31 | Dako | M0823, clone JC70/A | IF; IHC | Mouse anti-human | 1:200; 1:50 |
| CD31-PE | BD | 555446 | FC | Mouse anti-human | 1:10 |
| CD44-PE | BD | 550989 | FC | Mouse anti-human | 1:10 |
| CD45-PE | BD | 555483 | FC | Mouse anti-human | 1:10 |

TABLE 2-continued

| Antibody | Source | Catalog # | Purpose | Host Species & Reactivity | Concentration |
|---|---|---|---|---|---|
| CD73-PE | eBioscience | 12-0739-41 Clone AD2 | FC | Mouse anti-human | 1:10 |
| Cy3 | Sigma | C2181-1ML | IF | Sheep anti-mouse | 1:50 |
| Dapi | Roche | 10236276 | IF | Nucleus | 1:1,000 |
| eNOS | BD | 610297 | IF | Mouse anti-human | 1:100 |
| FITC | Sigma | F2883 | IF | Sheep anti-mouse | 1:50 |
| IgG-Alexa Fluor 488 | eBioscience | 53-4724-80 Clone eMB2a | FC | Mouse IgG Isotype control | 1:10 |
| IgG-FITC | BD | 554679 | FC | Mouse IgG Isotype Control | 1:10 |
| IgG-PE | BD | 555749 | FC | Mouse IgG Isotype Control | 1:10 |
| HRP-secondary | Dako | K4063 | IHC | HRP polymer anti-mouse | 1:1 |
| NG2 | Santa Cruz | sc-53389 | IF; IHC | Mouse anti-human | 1:100 |
| NG2-Alexa Fluor 488 | eBioscience | 53-6504-82 Clone 9.2.27 | FC; IF | Mouse anti-human | 1:10; 1:100 |
| PDGFRβ | Santa Cruz | SC-432 | IF | Rabbit anti-human | 1:100 |
| PDGFRβ-PE | R&D | FAB1263P | FC | Mouse anti-human | 1:10 |
| Tra-1-60-FITC | BD | 560380 | FC | Mouse anti-human | 1:10 |
| Tra-1-81-FITC | BD | 560194 | FC | Mouse anti-human | 1:10 |
| Ulex lectin | Vector Lab | FL-1061 | IF | Human ECs | 1:50 |
| VEcad | Santa Cruz | sc-9989 | IF | Mouse anti-human | 1:200 |
| VEcad-FITC | BD | 560411 | FC | Mouse anti-human | 1:10 |
| VEcad-PE | BD | 560410 | FC | Mouse anti-human | 1:10 |
| VEGFR2-PE | BD | 560494 | FC | Mouse anti-human | 1:10 |
| vWF | Dako | M0616 Clone F8/86 | IF | Mouse anti-human | 1:200 |

Real-Time Quantitative RT-PCR. Two-step reverse transcription polymerase chain reaction (RT-PCR) was performed on differentiated and undifferentiated (day 0) hPSCs as previously described in accordance with Applied Biosystems' instructions (Kusuma et al., 2012). For each primer set (VEcad, SMMHC, Tuj1, peripherin, ICAM, Id1, NOTCH1, NOTCH4, DLL4), we used the comparative computerized tomography method (Applied Biosystems) to calculate the amplification differences between different samples. The values for experiments were averaged and graphed with standard deviations.

Immunofluorescence. Cells were prepared for immunofluorescence as previously described (Kusuma et al., 2012). Briefly, fixed cells were blocked in 1% BSA, treated with 0.1% Triton-X (Sigma), and incubated with the antigen specific antibodies for the markers (see Table 2), followed by an appropriate secondary antibody, and DAPI (Roche Diagnostics) to label nuclei. The immunolabeled cells were examined using a fluorescent microscope (Olympus BX60).

EC Maturation. On day 12, derived EVCs were either sub-cultured in differentiation medium or sorted for VEcad+ cells. For this, EVCs were collected through digestion with Magnetic Activated Cell Sorting (MACS) buffer (0.5M EDTA and 1% BSA in PBS), incubated with 10 ul anti-human, PE-conjugated VEcad (BD) in MACS buffer for 45 minutes on ice, washed, incubated with 20 ul anti-PE microbeads (Miltenyi Biotec) in 80 ul MACS buffer for 15 minutes at 4° C., and washed twice. Cells were re-suspended in 500 µl MACS buffer and separated using a MS MACS separation column (Miltenyi Biotec). VEcad enrichment or depletion was confirmed by flow cytometry. Sorted cells were cultured on collage-type-IV-coated dishes for an additional 6 days in ECGM supplemented with 50 ng/ml VEGF and 10 µM SB431542. Media was changed every other day.

DiI-Labeled AC-LDL Uptake. Derived ECs were incubated with 10 µg/ml Dil-labeled Ac-LDL (Invitrogen) for 4 hours at 37° C., rinsed three times with PBS, fixed with 4% paraformaldehyde for 30 minutes, and visualized using a fluorescence microscope (Olympus).

Tumor Necrosis Factor Alpha (TNF-α) Activation. A previously established protocol for the activation of ECs was used (Dickinson et al., 2010). Briefly, cultured cells were stimulated for 24 hours with 10 ng/ml tumor necrosis factor-alpha (TNF-α; R&D) or blank as a control and analyzed for ICAM (Applied Biosystems).

Pericyte Maturation. We followed a published protocol for pericyte maturation (Orlidge and D'Amore, 1987). On day 12, derived EVCs were collected through digestion with TrypLE and re-plated on tissue culture treated 6 well plates in media comprised of DMEM and 10% FBS. After 2-3 hours, unattached cells were removed and media was replaced. Cells were cultured for 6 days, changing the media every second day.

Mesenchymal Differentiation (Adipogenic and Osteogenic). For adipogenic differentiation (Pittenger et al., 1999), we cultured derived pericytes at 10,000 cells/cm$^2$ in media comprised of DMEM, 10% FBS, 1% Penicillin/Streptomycin, 200 µM Indomethacin, 500 µM 3-Isobutyl-1-methyl xanthine (IBMX), and 5 µg/ml Insulin (all from Sigma) for 4 weeks. To assess adipogenic potential, cells were fixed with 3.7% formaldehyde, and then dehydrated with 60% isopropanol for 5 minutes. Cells were incubated with Oil Red O (Sigma) at 1.8 mg/ml in 60/40 isopropanol/DI $H_2O$, for 10 minutes and imaged using an inverted light microscope (Olympus).

For osteogenic differentiation (Grayson et al., 2010), we cultured derived pericytes at 5,000 cells/cm$^2$ in media comprised of low glucose DMEM, 10% FBS, 1% Penicillin/Streptomycin, 10 mM β-glycerophosphate, 100 nM dexamethasone, and 50 µM ascorbic acid (all from Sigma) for 2 weeks. Media were prepared fresh weekly. To assess osteogenic potential, samples were fixed with 3.7% formaldehyde, and washed with DI $H_2O$, Samples were incubated with Alizarin Red S (40 mM in DI $H_2O$, pH ~4.2; Sigma) for 10-20 minutes.

Collagen Gel Assay. Collagen gels (7.1 mg/ml, BD Biosciences) were prepared as previously described (Abaci et al., 2011). EVCs, VEcad+, or VEcad-cells were encapsulated at a density of 2 million cells/ml. ECGM supplemented with 50 ng/ml VEGF was added to the gels after 30 minutes at 37° C. in a $CO_2$ incubator. Visualization and image acquisition were performed using an inverted light microscope (Olympus).

Synthesis of HA Gels. Acrylated hyaluronic acid (HA) hydrogels were prepared as previously reported (Hanjaya-Putra et al., 2011; Khetan and Burdick, 2010; Khetan et al., 2009). Derived EVCs were encapsulated in HA hydrogels at a density of $4 \times 10^6$ cells/ml and cultured for up to three days in endothelial growth media 2 (EGM2; Lonza). Visualization and image acquisition were performed using an inverted light microscope (Olympus) and a confocal microscope (LSM 510 Meta; Carl Zeiss, Inc.) along the culture. We performed FM-464 vacuole staining (Invitrogen) following the manufacturer's protocol (Hanjaya-Putra et al., 2011). To test parallel differentiation, EVCs were also cultured in adherent culture in EGM 2 (Lonza) for 3 days with media changed daily.

Subcutaneous Implantation of Cells. PSC-derived cells were labeled with PKH-26 (red) according to the manufacturer's protocol and as previously (Wanjare et al., 2012). PKH-26 labeled cells, which were re-suspended with Matrigel (BD Biosciences) and 50 ng/ml bFGF or engineered vascular networks in HA gels for 3 days were implanted subcutaneously into nude 6-8 week old female mice in quadruplicate. To visualize angiogenesis in the implants prior to sample removal after 2 weeks, we injected Alexa Fluor® 488 (or, in some instances, Alexa Fluor® 647) conjugated isolectin GS-IB4 from *Griffonia simplicifolia* (Invitrogen) through the tail veins of the mice (Kang et al., 2011). After 20 minutes, mice were euthanized by $CO_2$ asphyxiation and the explants were harvested and fixed in 3.7 percent formaldehyde (Sigma) and proceeded for visualization and sectioning. The Johns Hopkins University Institutional Animal Care and Use Committee approved all animal protocols.

Histology. The fixed explants were dehydrated in graded ethanol (70%-100%), embedded in paraffin, serially sectioned using a microtome (5 µm), and stained with immunohistochemistry for anti-human CD31 (Dako) and anti-human NG2 (Santa Cruz) (Hanjaya-Putra et al., 2011; Mead et al., 2007). Mouse tissue was used as controls. Blood vessels containing human CD31 cells were counted and measured using ImageJ (NIH). We sampled a minimum of 6 images for each construct.

Graphs and Statistics. All analyses were performed in triplicate samples for n=3 at least. Real-time RT-PCR were also performed on triplicate samples (n=3) with triplicate readings. One Way ANOVA with Bonferroni post-hoc test were performed to determine significance (GraphPad Prism 4.02).

The following claims are thus to be understood to include what is specifically illustrated and described above, what is conceptually equivalent, what can be obviously substituted and also what incorporates the essential idea of the invention. The illustrated embodiment has been set forth only for the purposes of example and that should not be taken as limiting the invention. Therefore, it is to be understood that, within the scope of the appended claims, the invention may be practiced other than as specifically described herein.

References

Incorporated Herein by Reference to the Extent Permissible by Applicable Laws and Rules Abaci, H. E., Truitt, R., Tan, S., and Gerecht, S. (2011). Unforeseen decreases in dissolved oxygen levels affect tube formation kinetics in collagen gels. American Journal of Physiology—Cell Physiology 301, C431-C440.

Airas, L., Hellman, J., Salmi, M., Bono, P., Puurunen, T., Smith, D. J., and Jalkanen, S. (1995). CD73 is involved in lymphocyte binding to the endothelium: characterization of lymphocyte-vascular adhesion protein 2 identifies it as CD73. The Journal of Experimental Medicine 182, 1603-1608.

Bardin, N., Anfosso, F., MassÃ©, J. M., Cramer, E., Sabatier, F., Bivic, A. L., Sampol, J., and Dignat-George, F. (2001). Identification of CD146 as a component of the endothelial junction involved in the control of cell-cell cohesion. Blood 98, 3677-3684.

Cheng, L., Hansen, Nancy F., Zhao, L., Du, Y., Zou, C., Donovan, Frank X., Chou, B.-K., Zhou, G., Li, S., Dowey, Sarah N., et al. (2012). Low Incidence of DNA Sequence Variation in Human Induced Pluripotent Stem Cells Generated by Nonintegrating Plasmid Expression. Cell Stem Cell 10, 337-344.

Cheng, L., Hansen, Nancy F., Zhao, L., Du, Y., Zou, C., Donovan, Frank X., Chou, B.-K., Zhou, G., Li, S., Dowey, Sarah N., et al. (2012). Low Incidence of DNA Sequence Variation in Human Induced Pluripotent Stem Cells Generated by Nonintegrating Plasmid Expression. Cell Stem Cell 10, 337-344.

Chou, B. K., Mali, P., Huang, X., Ye, Z., Dowey, S. N., Resar, L. M. S., Zou, C., Zhang, Y. A., Tong, J., and Cheng, L. (2011). Efficient human iPS cell derivation by a non-integrating plasmid from blood cells with unique epigenetic and gene expression signatures. Cell Research 21, 518-529.

Crisan, M., Corselli, M., Chen, W. C. W., and Peault, B. (2012). Perivascular cells for regenerative medicine. Journal of Cellular and Molecular Medicine, n/a-n/a.

Crisan, M., Yap, S., Casteilla, L., Chen, C. W., Corselli, M., Park, T. S., Andriolo, G., Sun, B., Zheng, B., Zhang, L., et al. (2008). A Perivascular Origin for Mesenchymal Stem Cells in Multiple Human Organs. Cell Stem Cell 3, 301-313.

Dar, A., Domev, H., Ben-Yosef, O., Tzukerman, M., Zeevi-Levin, N., Novak, A., Germanguz, I., Amit, M., and Itskovitz-Eldor, J. (2011). Multipotent Vasculogenic Pericytes From Human Pluripotent Stem Cells Promote Recovery of Murine Ischemic Limb/Clinical Perspective. Circulation 125, 87-99.

Dickinson, L. E., Moura, M. E., and Gerecht, S. (2010). Guiding endothelial progenitor cell tube formation using patterned fibronectin surfaces. Soft Matter 6, 5109-5119.

Discher, D. E., Mooney, D. J., and Zandstra, P. W. (2009). Growth Factors, Matrices, and Forces Combine and Control Stem Cells. Science 324, 1673-1677.

Drukker, M., Tang, C., Ardehali, R., Rinkevich, Y., Seita, J., Lee, A. S., Mosley, A. R., Weissman, I. L., and Soen, Y. (2012). Isolation of primitive endoderm, mesoderm, vascular endothelial and trophoblast progenitors from human pluripotent stem cells. Nature Biotechnology 30, 531-542.

Duff, S. E., Li, C., Garland, J. M., and Kumar, S. (2003). CD105 is important for angiogenesis: Evidence and potential applications. FASEB Journal 17, 984-992.

Ferreira, L. S., Gerecht, S., Shieh, H. F., Watson, N., Rupnick, M. A., Dallabrida, S. M., Vunjak-Novakovic, G., and Langer, R. (2007). Vascular progenitor cells isolated from human embryonic stem cells give rise to endothelial and smooth muscle-like cells and form vascular networks in vivo. Circulation Research 101, 286-294.

Grayson, W. L., Frohlich, M., Yeager, K., Bhumiratana, S., Chan, M. E., Cannizzaro, C., Wan, L. Q., Liu, X. S., Guo, X. E., and Vunjak-Novakovic, G. (2010). Engineering anatomically shaped human bone grafts. Proceedings of the National Academy of Sciences of the United States of America 107, 3299-3304.

Haase, A., Olmer, R., Schwanke, K., Wunderlich, S., Merkert, S., Hess, C., Zweigerdt, R., Gruh, I., Meyer, J., Wagner, S., et al. (2009). Generation of Induced Pluripotent Stem Cells from Human Cord Blood. Cell Stem Cell 5, 434-441.

Hanjaya-Putra, D., Bose, V., Shen, Y. I., Yee, J., Khetan, S., Fox-Talbot, K., Steenbergen, C., Burdick, J. A., and Gerecht, S. (2011). Controlled activation of morphogenesis to generate a functional human microvasculature in a synthetic matrix. Blood 118, 804-815.

Hofmann, J. J., and Iruela-Arispe, M. L. (2007). Notch Signaling in Blood Vessels: Who Is Talking to Whom About What? Circulation Research 100, 1556-1568.

James, D., Nam, H. S., Seandel, M., Nolan, D., Janovitz, T., Tomishima, M., Studer, L., Lee, G., Lyden, D., Benezra, R., et al. (2010). Expansion and maintenance of human embryonic stem cell-derived endothelial cells by TGFb inhibition is Id1 dependent. Nature Biotechnology 28, 161-166.

Kang, K.-T., Allen, P., and Bischoff, J. (2011). Bioengineered human vascular networks transplanted into secondary mice reconnect with the host vasculature and re-establish perfusion. Blood.

Khetan, S., and Burdick, J. A. (2010). Patterning network structure to spatially control cellular remodeling and stem cell fate within 3-dimensional hydrogels. Biomaterials 31, 8228-8234.

Khetan, S., Katz, J. S., and Burdick, J. A. (2009). Sequential crosslinking to control cellular spreading in 3-dimensional hydrogels. Soft Matter 5, 1601-1606.

Kusuma, S., Zhao, S., and Gerecht, S. (2012). The extracellular matrix is a novel attribute of endothelial progenitors and of hypoxic mature endothelial cells. The FASEB Journal.

Lee, G., Chambers, S. M., Tomishima, M. J., and Studer, L. (2010). Derivation of neural crest cells from human pluripotent stem cells. Nat Protocols 5, 688-701.

Mali, P., Chou, B. K., Yen, J., Ye, Z., Zou, J., Dowey, S., Brodsky, R. A., Ohm, J. E., Yu, W., Baylin, S. B., et al. (2010). Butyrate greatly enhances derivation of human induced pluripotent stem cells by promoting epigenetic remodeling and the expression of pluripotency-associated genes. Stem Cells 28, 713-720.

Mead, L. E., Prater, D., Yoder, M. C., and Ingram, D. A. (2007). Isolation and Characterization of Endothelial Progenitor Cells from Human Blood. In Current Protocols in Stem Cell Biology (John Wiley & Sons, Inc.).

Orlidge, A., and D'Amore, P. A. (1987). Inhibition of capillary endothelial cell growth by pericytes and smooth muscle cells. The Journal of Cell Biology 105, 1455-1462.

Park, S.-W., Jun Koh, Y., Jeon, J., Cho, Y.-H., Jang, M.-J., Kang, Y., Kim, M.-J., Choi, C., Sook Cho, Y., Chung, H.-M., et al. (2010). Efficient differentiation of human pluripotent stem cells into functional CD34+ progenitor cells by combined modulation of the MEK/ERK and BMP4 signaling pathways. Blood 116, 5762-5772.

Pittenger, M. F., Mackay, A. M., Beck, S. C., Jaiswal, R. K., Douglas, R., Mosca, J. D., Moorman, M. A., Simonetti, D. W., Craig, S., and Marshak, D. R. (1999). Multilineage potential of adult human mesenchymal stem cells. Science 284, 143-147.

Sainson, R. A., and Harris, A. (2008). Regulation of angiogenesis by homotypic and heterotypic notch signalling in endothelial cells and pericytes: from basic research to potential therapies. Angiogenesis 11, 41-51.

Stewart, K. S., Zhou, Z., Zweidler-McKay, P., and Kleinerman, E. S. (2011). Delta-like ligand 4-Notch signaling regulates bone marrow-derived pericyte/vascular smooth muscle cell formation. Blood 117, 719-726.

Stratman, A. N., Malotte, K. M., Mahan, R. D., Davis, M. J., and Davis, G. E. (2009a). Pericyte recruitment during vasculogenic tube assembly stimulates endothelial basement membrane matrix formation. Blood 114, 5091-5101.

Stratman, A. N., Saunders, W. B., Sacharidou, A., Koh, W., Fisher, K. E., Zawieja, D. C., Davis, M. J., and Davis, G. E. (2009b). Endothelial cell lumen and vascular guidance tunnel formation requires MT1-MMP-dependent proteolysis in 3-dimensional collagen matrices. Blood 114, 237-247.

Thomson, J. A. (1998). Embryonic stem cell lines derived from human blastocysts. Science 282, 1145-1147.

Vo, E., Hanjaya-Putra, D., Zha, Y., Kusuma, S., and Gerecht, S. (2010). Smooth-Muscle-Like Cells Derived from Human Embryonic Stem Cells Support and Augment Cord-Like Structures In Vitro. Stem Cell Reviews and Reports 6, 237-247.

Vodyanik, M. A., Yu, J., Zhang, X., Tian, S., Stewart, R., Thomson, J. A., and Slukvin, I. I. (2010). A mesoderm-derived precursor for mesenchymal stem and endothelial cells. Cell Stem Cell 7, 718-729.

Vunjak-Novakovic, G., and Scadden, David T. (2011). Biomimetic Platforms for Human Stem Cell Research. Cell Stem Cell 8, 252-261.

Wang, Z. Z., Au, P., Chen, T., Shao, Y., Daheron, L. M., Bai, H., Arzigian, M., Fukumura, D., Jain, R. K., and Scadden, D. T. (2007). Endothelial cells derived from human embryonic stem cells form durable blood vessels in vivo. Nat Biotech 25, 317-318.

Wanjare, M., Kuo, F., and Gerecht, S. (2012). Derivation and maturation of synthetic and contractile vascular smooth muscle cells from human pluripotent stem cells. Cardiovascular Research.

Yang, L., Soonpaa, M. H., Adler, E. D., Roepke, T. K., Kattman, S. J., Kennedy, M., Henckaerts, E., Bonham, K., Abbott, G. W., Linden, R. M., et al. (2008). Human cardiovascular progenitor cells develop from a KDR+ embryonic-stem-cell-derived population. Nature 453, 524-528.

Zou, J., Mali, P., Huang, X., Dowey, S. N., and Cheng, L. (2011). Site-specific gene correction of a point mutation in human iPS cells derived from an adult patient with sickle cell disease. Blood 118, 4599-4608.

What is claimed is:

1. A method for differentiating human embryonic stem cells (hESCs) or human induced pluripotent stem cells (hiPSCs) into early vascular cells (EVCs) in vitro, comprising the steps of:
   plating a single-cell suspension of hESCs or hiPSCs onto a surface coated with suitable materials selected from the group consisting of type I collagen, fibronectin, and type IV collagen;
   adding culture medium;
   culturing the cells for several days;

adding Vascular Endothelial Growth Factor (VEGF) and a transforming growth factor-beta (TGF-β) inhibitor to the culture medium;

culturing the cells for several days; and harvesting the resulting EVCs, wherein said EVCs express CD73 and one or more of CD105 and CD146.

2. The method for differentiating of claim 1, wherein the TGF β inhibitor is SB431542.

3. The method for differentiating of claim 1, wherein the concentration of VEGF is between about 1 and 50 ng/ml.

4. The method for differentiating of claim 1, wherein the suitable material is type IV collagen.

5. The method for differentiating of claim 1, wherein the media used for culturing are supplemented with serum.

6. The method for differentiating of claim 5, wherein the media are supplemented with 10% serum.

7. The method for differentiating of claim 1, wherein prior to the step of adding VEGF the cells are harvested from the surface and then plated onto a surface coated with the suitable materials with VEGF in the culture medium.

8. The method for differentiating of claim 1, further comprising a step of embedding the harvested resulting EVC cells in a matrix following the step of harvesting.

9. The method for differentiating of claim 8, wherein after embedding the harvested resulting EVC cells in a matrix, the cells comprise a population that can self-organize into vascular networks.

10. The method for differentiating of claim 9, wherein the matrix is a hydrophilic matrix.

11. The method for differentiating of claim 10, wherein the hydrophilic matrix is a hydrogel selected from the group consisting of hyaluronic acid (HA) hydrogel and collagen hydrogel.

12. The method for differentiating of claim 8, wherein the matrix is a hydrophilic matrix.

13. The method for differentiating of claim 12, wherein the hydrophilic matrix is a hydrogel selected from the group consisting of hyaluronic acid (HA) hydrogel and collagen hydrogel.

14. The method for differentiating of claim 1, further comprising the step of sub-culturing the EVCs in a medium containing serum on a tissue-culture treated surface and removing unattached cells after 4 hours.

15. The method for differentiating of claim 14, wherein the medium for sub-culturing EVCs also contains Angiopoietin 1 or TGFb-1.

* * * * *

UNITED STATES PATENT AND TRADEMARK OFFICE
CERTIFICATE OF CORRECTION

PATENT NO. : 9,506,037 B2
APPLICATION NO. : 13/844313
DATED : November 29, 2016
INVENTOR(S) : Sharon Gerecht and Sravanti Kusuma Page 1 of 1

It is certified that error appears in the above-identified patent and that said Letters Patent is hereby corrected as shown below:

In the Specification

Column 1, Lines 5-12, please replace the first paragraph as follows:
STATEMENT OF GOVERNMENTAL INTEREST
This invention was made with government support under grant numbers HL112644, HL073781, HL107938, CA143868, awarded by the National Institutes of Health, and grant number 1054415, awarded by the National Science Foundation. The government has certain rights in the invention.

Signed and Sealed this
Thirteenth Day of February, 2018

Andrei Iancu
*Director of the United States Patent and Trademark Office*